(12) United States Patent
Shalev et al.

(10) Patent No.: US 7,684,859 B2
(45) Date of Patent: Mar. 23, 2010

(54) STIMULATION OF THE OTIC GANGLION FOR TREATING MEDICAL CONDITIONS

(75) Inventors: Alon Shalev, Ra'anana (IL); Yossi Gross, Moshav Mazor (IL)

(73) Assignee: Brainsgate Ltd., Ra'Anana (IL)

( * ) Notice: Subject to any disclaimer, the term of this patent is extended or adjusted under 35 U.S.C. 154(b) by 339 days.

(21) Appl. No.: 11/668,305

(22) Filed: Jan. 29, 2007

(65) Prior Publication Data

US 2008/0033509 A1 Feb. 7, 2008

Related U.S. Application Data

(63) Continuation-in-part of application No. 10/535,024, filed as application No. PCT/IL03/00966 on Nov. 13, 2003, application No. 11/668,305, which is a continuation-in-part of application No. 10/512,780, filed as application No. PCT/IL03/00338 on Apr. 25, 2003, now abandoned.

(60) Provisional application No. 60/376,048, filed on Apr. 25, 2002, provisional application No. 60/461,232, filed on Apr. 8, 2003, provisional application No. 60/426,180, filed on Nov. 14, 2002.

(51) Int. Cl.
*A61N 1/00* (2006.01)

(52) U.S. Cl. .......................................................... 607/2

(58) Field of Classification Search ...................... 607/2, 607/3, 43–58
See application file for complete search history.

(56) References Cited

U.S. PATENT DOCUMENTS

| 4,666,829 A | 5/1987 | Glenner et al. |
|---|---|---|
| 4,866,042 A | 9/1989 | Neuwelt |
| 4,874,694 A | 10/1989 | Gandy et al. |
| 4,886,493 A | 12/1989 | Yee |
| 4,979,511 A | 12/1990 | Terry, Jr. et al. |

(Continued)

FOREIGN PATENT DOCUMENTS

EP 1 559 369 A1 8/2005

(Continued)

OTHER PUBLICATIONS

Japanese Office Action dated Sep. 16, 2008, which issued during the prosecution of Applicant's Japanese Patent Application No. 2001-581749.

(Continued)

*Primary Examiner*—Scott M Getzow
(74) *Attorney, Agent, or Firm*—RatnerPrestia

(57) ABSTRACT

Apparatus is provided including one or more electrodes, adapted to be applied to an otic-ganglion site of a patient selected from the group consisting of: an otic ganglion, an associated neural tract of the otic ganglion, an afferent fiber going into the otic ganglion, and an efferent fiber going out of the otic ganglion. The apparatus further includes a stimulator, configured to drive the one or more electrodes to apply a current to the otic-ganglion site, and to configure the current to activate the otic-ganglion site sufficiently to induce at least one effect selected from the group consisting of: a change in cerebral blood flow (CBF) of the patient, and a change in permeability of a blood-brain-barrier (BBB) of the patient. Other embodiments are also described.

35 Claims, 5 Drawing Sheets

U.S. PATENT DOCUMENTS

| | | | |
|---|---|---|---|
| 5,011,472 A | 4/1991 | Aebischer et al. |
| 5,031,618 A | 7/1991 | Mullett |
| 5,059,415 A | 10/1991 | Neuwelt |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. et al. |
| 5,215,086 A | 6/1993 | Terry, Jr. et al. |
| 5,215,089 A | 6/1993 | Baker, Jr. |
| 5,222,494 A | 6/1993 | Baker, Jr. et al. |
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,268,164 A | 12/1993 | Kozarich et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,639,853 A | 6/1997 | Paradiso et al. |
| 5,707,400 A | 1/1998 | Terry, Jr. et al. |
| 5,725,471 A | 3/1998 | Davey et al. |
| 5,752,515 A | 5/1998 | Jolesz et al. |
| 5,756,071 A | 5/1998 | Mattern et al. |
| 5,792,100 A | 8/1998 | Shantha |
| 5,830,670 A | 11/1998 | De la Monte et al. |
| 5,833,988 A | 11/1998 | Friden |
| 5,849,600 A | 12/1998 | Nixon et al. |
| 5,855,907 A | 1/1999 | Peyman |
| 5,928,272 A | 7/1999 | Adkins et al. |
| 5,938,689 A | 8/1999 | Fischell et al. |
| 5,938,690 A | 8/1999 | Law et al. |
| 5,981,194 A | 11/1999 | Jefferies et al. |
| 5,985,581 A | 11/1999 | Nixon et al. |
| 6,001,331 A | 12/1999 | Caprathe et al. |
| 6,005,004 A | 12/1999 | Katz et al. |
| 6,006,124 A | 12/1999 | Fischell et al. |
| 6,016,449 A | 1/2000 | Fischell et al. |
| 6,061,593 A | 5/2000 | Fischell et al. |
| 6,066,163 A | 5/2000 | John |
| 6,071,705 A | 6/2000 | Wands et al. |
| 6,086,525 A | 7/2000 | Davey et al. |
| 6,087,118 A | 7/2000 | Aronson et al. |
| 6,114,175 A | 9/2000 | Klunk et al. |
| 6,117,454 A | 9/2000 | Kreuter et al. |
| 6,128,538 A | 10/2000 | Fischell et al. |
| 6,130,048 A | 10/2000 | Nixon |
| 6,132,977 A | 10/2000 | Thompson et al. |
| 6,134,474 A | 10/2000 | Fischell et al. |
| 6,161,045 A | 12/2000 | Fischell et al. |
| 6,200,768 B1 | 3/2001 | Mandelkow et al. |
| 6,210,895 B1 | 4/2001 | Schipper et al. |
| 6,211,235 B1 | 4/2001 | Wu et al. |
| 6,230,049 B1 | 5/2001 | Fischell et al. |
| 6,232,326 B1 | 5/2001 | Nelson |
| 6,238,892 B1 | 5/2001 | Mercken et al. |
| 6,277,841 B1 | 8/2001 | Rajagopalan et al. |
| 6,287,793 B1 | 9/2001 | Schenk et al. |
| 6,322,494 B1 | 11/2001 | Bullivant et al. |
| 6,325,475 B1 | 12/2001 | Hayes et al. |
| 6,329,531 B1 | 12/2001 | Turner et al. |
| 6,338,715 B1 | 1/2002 | Hayes et al. |
| 6,353,754 B1 | 3/2002 | Fischell et al. |
| 6,354,299 B1 | 3/2002 | Fischell et al. |
| 6,358,681 B2 | 3/2002 | Ginsberg et al. |
| 6,360,122 B1 | 3/2002 | Fischell et al. |
| 6,405,079 B1 | 6/2002 | Ansarinia |
| 6,410,046 B1 | 6/2002 | Lerner |
| 6,415,184 B1 | 7/2002 | Ishikawa et al. |
| 6,427,086 B1 | 7/2002 | Fischell et al. |
| 6,432,986 B2 | 8/2002 | Levin |
| 6,459,936 B2 | 10/2002 | Fischell et al. |
| 6,466,822 B1 | 10/2002 | Pless et al. |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 * | 2/2003 | Ansarinia ............... 607/46 |
| 6,529,774 B1 | 3/2003 | Greene |
| 6,531,454 B1 | 3/2003 | Leary et al. |
| 6,587,719 B1 | 7/2003 | Barrett et al. |
| 6,587,724 B2 | 7/2003 | Mann |
| 6,591,137 B1 | 7/2003 | Fischell et al. |
| 6,591,138 B1 | 7/2003 | Fischell et al. |
| 6,597,953 B2 | 7/2003 | Boling |
| 6,597,954 B1 | 7/2003 | Pless et al. |
| 6,606,521 B2 | 8/2003 | Paspa et al. |
| 6,609,025 B2 | 8/2003 | Barrett et al. |
| 6,609,032 B1 | 8/2003 | Woods et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry et al. |
| 6,622,047 B2 | 9/2003 | Barrett et al. |
| 6,647,296 B2 | 11/2003 | Fischell et al. |
| 6,662,035 B2 | 12/2003 | Sochor |
| 6,678,553 B2 | 1/2004 | Lerner et al. |
| 6,690,974 B2 | 2/2004 | Archer et al. |
| 6,735,474 B1 | 5/2004 | Loeb et al. |
| 6,810,285 B2 | 10/2004 | Pless et al. |
| 6,811,788 B2 | 11/2004 | Yu |
| 6,853,858 B2 * | 2/2005 | Shalev ............... 607/3 |
| 6,905,827 B2 | 6/2005 | Wohlgemuth et al. |
| 6,922,590 B1 | 7/2005 | Whitehurst |
| 2001/0004644 A1 | 6/2001 | Levin |
| 2001/0014670 A1 | 8/2001 | Balin et al. |
| 2001/0018191 A1 | 8/2001 | Mercken et al. |
| 2001/0020097 A1 | 9/2001 | Audia et al. |
| 2001/0026916 A1 | 10/2001 | Ginsberg et al. |
| 2001/0027309 A1 | 10/2001 | Elsberry |
| 2001/0044126 A1 | 11/2001 | Holtzman et al. |
| 2001/0047014 A1 | 11/2001 | Alanine et al. |
| 2001/0051633 A1 | 12/2001 | Bigge et al. |
| 2002/0002270 A1 | 1/2002 | Zinkowski et al. |
| 2002/0006627 A1 | 1/2002 | Reitz et al. |
| 2002/0009445 A1 | 1/2002 | Du et al. |
| 2002/0019016 A1 | 2/2002 | Vanmechelen et al. |
| 2002/0019412 A1 | 2/2002 | Andersen et al. |
| 2002/0019519 A1 | 2/2002 | Bingham et al. |
| 2002/0022242 A1 | 2/2002 | Small et al. |
| 2002/0022593 A1 | 2/2002 | Yue |
| 2002/0022621 A1 | 2/2002 | Chaturvedula et al. |
| 2002/0022650 A1 | 2/2002 | Posmantur et al. |
| 2002/0025955 A1 | 2/2002 | Han et al. |
| 2002/0026652 A1 | 2/2002 | Allen et al. |
| 2002/0028462 A1 | 3/2002 | Tanzi et al. |
| 2002/0028834 A1 | 3/2002 | Villalobos et al. |
| 2002/0035145 A1 | 3/2002 | Tsai et al. |
| 2002/0040032 A1 | 4/2002 | Glasky et al. |
| 2002/0040052 A1 | 4/2002 | Ito et al. |
| 2002/0042121 A1 | 4/2002 | Riesner et al. |
| 2002/0042420 A1 | 4/2002 | Briem et al. |
| 2002/0044919 A1 | 4/2002 | Yu |
| 2002/0052311 A1 | 5/2002 | Solomon et al. |

| | | |
|---|---|---|
| 2002/0055501 A1 | 5/2002 | Olson et al. |
| 2002/0066959 A1 | 6/2002 | Joshi |
| 2002/0068080 A1 | 6/2002 | Lerner |
| 2002/0082583 A1 | 6/2002 | Lerner |
| 2002/0099412 A1 | 7/2002 | Fischell et al. |
| 2002/0099417 A1 | 7/2002 | Naritoku et al. |
| 2002/0123678 A1 | 9/2002 | Lerner et al. |
| 2002/0133841 A1 | 9/2002 | Leviten |
| 2002/0169307 A1 | 11/2002 | Klein |
| 2002/0169485 A1 | 11/2002 | Pless et al. |
| 2002/0183683 A1 | 12/2002 | Lerner |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0036781 A1 | 2/2003 | Nuttin et al. |
| 2003/0050527 A1 | 3/2003 | Fox et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0079742 A1 | 5/2003 | Giroux |
| 2003/0106083 A1 | 6/2003 | Allen |
| 2003/0131367 A1 | 7/2003 | Guenther et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176892 A1 | 9/2003 | Shalev |
| 2003/0176898 A1 | 9/2003 | Gross et al. |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0191426 A1 | 10/2003 | Lerner et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook et al. |
| 2004/0054297 A1 | 3/2004 | Wingeier et al. |
| 2004/0133248 A1 | 7/2004 | Frei et al. |
| 2004/0136950 A1 | 7/2004 | Ni et al. |
| 2004/0136951 A1 | 7/2004 | Ni et al. |
| 2004/0153129 A1 | 8/2004 | Pless et al. |
| 2004/0210269 A1 | 10/2004 | Shalev et al. |
| 2004/0220644 A1 | 11/2004 | Shalev et al. |
| 2005/0020519 A1 | 1/2005 | Albiston et al. |
| 2005/0054939 A1 | 3/2005 | Ben-Ari et al. |
| 2005/0074506 A1 | 4/2005 | Natan et al. |
| 2005/0112090 A9 | 5/2005 | Ni et al. |
| 2005/0118187 A1 | 6/2005 | Yu |
| 2005/0137646 A1 | 6/2005 | Wallace et al. |
| 2005/0137647 A1 | 6/2005 | Wallace et al. |
| 2005/0159790 A1 | 7/2005 | Shalev et al. |
| 2005/0177514 A1 | 8/2005 | Sasselli |
| 2006/0195169 A1 | 8/2006 | Gross |
| 2006/0287677 A1 | 12/2006 | Shalev |

FOREIGN PATENT DOCUMENTS

| | | |
|---|---|---|
| JP | 08-229141 | 9/1996 |
| WO | WO 93/09841 | 5/1993 |
| WO | WO 93/25271 | 12/1993 |
| WO | WO 97/18855 | 5/1997 |
| WO | WO 99/03473 | 1/1999 |
| WO | WO 00/44432 | 8/2000 |
| WO | WO 00/73343 A2 | 12/2000 |
| WO | WO 01/43733 A2 | 6/2001 |
| WO | WO 01/85094 A2 | 11/2001 |
| WO | WO 01/97905 A1 | 12/2001 |
| WO | WO 02/32504 A2 | 4/2002 |
| WO | WO 02/068029 A2 | 9/2002 |
| WO | WO 02/068031 A2 | 9/2002 |
| WO | WO 02/094191 A2 | 11/2002 |
| WO | WO 03/000310 A2 | 1/2003 |
| WO | WO 03/020350 A1 | 3/2003 |
| WO | WO 03/063959 A1 | 8/2003 |
| WO | WO 03/084591 A1 | 10/2003 |
| WO | WO 03/090599 A2 | 11/2003 |
| WO | WO 03/105658 A2 | 12/2003 |
| WO | WO 2004/010923 A2 | 2/2004 |
| WO | WO 2004/043217 A2 | 5/2004 |
| WO | WO 2004/043218 A2 | 5/2004 |
| WO | WO 2004/043334 A2 | 5/2004 |
| WO | WO 2004/044947 A2 | 5/2004 |
| WO | WO 2004/045242 A2 | 5/2004 |
| WO | WO 2004/064918 A1 | 8/2004 |
| WO | WO 2005/030025 A2 | 4/2005 |
| WO | WO 2005/030118 A2 | 4/2005 |
| WO | WO 2006/021957 A2 | 3/2006 |

OTHER PUBLICATIONS

Suzuki et al.; "Effect on cortical blood flow of electrical stimulation of trigeminal cerebrovascular nerve fibres in the rat"; Acta Physio Scand 1990, 138, 307-315.

Major et al.; "Odorants Presented to the Rat Nasal Cavity Increase Cortical Blood Flow"; Chem. Senses 24: 665-669, 1999.

Fusco et al.; "'Capsaicin-Sensitive' Sensory Neurons in Cluster Headache: Pathophysiological Aspects and Therapeutic Indication"; Headache, 34, 132-137, 1994.

Lambert et al.; "Decreased carotid arterial resistance in cats in response to trigeminal stimulation"; Journal of Neurosurgery, 61, 307-315, 1984.

Silver; "Neural and Pharmacological Basis for Nasal Irritation"; Annals New York Academy of Sciences, 152-163, 1992.

Sikic et al.; "Modulation and prevention of multidrug resistance by inhibitors of P-glycoprotein"; Cancer Chemother Pharmacol (1997) 40 (Suppl.): S13-S-19.

Fu et al.; "Improved bioavailability of orally administered drugs by Chinese herbal enhancers through modulation of P-glycoprotein"; ASHP 39th Midyear Clinical Meeting and Exhibits, Dec. 5-9, 2004, Orlando, FL, Presentation Abstracts.

Delepine et al.; "Plasma Protein Extravasation Induced in the Rat Dura Mater by Stimulation of the Parasympathetic Sphenopalatine Ganglion"; Experimental Neurology, 147, 389-400, 1997.

Hara et al.; "Parasympathetic Cerebrovascular Innervation: An Anterograde Tracing from the Spenopalatine Ganglion in the Rat"; Neurosurgery, vol. 32, No. 5, May 1993, 822-827.

Ruskell; "The orbital branches of the pterygopalatine ganglion and their relationship with internal carotid nerve brances in primates"; J. Anat. 1970, 106, 2, 323-339.

Kroll et al; "Outwitting the Blood-Brain Barrier for Therapeutic Purposes: Osmotic Opening and Other Means"; Neurosurgery, vol. 42, No. 5, May 1998, 1083-1100.

Sanders et al; "Efficacy of spenopalatine ganglion blockade in 66 patients suffering from cluster headache: a 12- to 70-month follow-up evaluation"; J. Neurosurg., vol. 87, Dec. 1997, 876-880.

Suzuki et al; "Selective Electrical Stimulations of Postganglionic Cerebrovascular Parasympathetic Nerve Fibers Originating from the Sphenopalatine Ganglion Enhances Cortical Blood Flow in the Rat"; Journal of Cerebral Blood Flow and Metabolism, 10:383-391, 1990.

Samad et al.; "Interluken-1beta-mediated induction of Cox-2 in the CNS contributes to inflammatory pain hypersensitivity"; Nature, vol. 410, Mar. 22, 2001, 471-475.

Van de Waterbeemd et al.; "Estimation of Blood-Brain Barrier Crossing of Drugs Using Molecular Size and Shape, and H-Bonding Descriptors"; Journal of Drug Targeting, 6, 151-165, 1998.

Young; "Electrical stimulation of the trigeminal nerve root for the treatment of chronic facial pain"; J Neurosurg 83:72-78, 1995.

Suzuki et al.; "Origins and Pathways of Cerebrovascular Vasoactive Intestinal Polypeptide-Positive Nerves in Rat"; Journal of Cerebral Blood Flow and Metabolism, vol. 8 No. 5, 697-712, 1988.

U.S. Appl. No. 60/364,451.
U.S. Appl. No. 60/368,657.
U.S. Appl. No. 10/522,615.
U.S. Appl. No. 60/426,181.
U.S. Appl. No. 10/525,025.
U.S. Appl. No. 60/448,807.
U.S. Appl. No. 60/461,232.
U.S. Appl. No. 60/506,165.
U.S. Appl. No. 60/604,037.

Hotta H et al., in an article entitled, "Effects of stimulating the nucleus basalis of Meynert on blood flow and delayed neuronal death following transient ischemia in rat cerebral cortes," Jap J Phys 52:383-393 (2002).

Segher O et al., in an article entitled, "Spinal cord stimulation reducing infract volume in model of focal cerebral ischemia in rats," J Neurosurg 99(1):131-137 (2003).

Goadsby PJ et al., "Effect of stimulation of trigeminal ganglion on regional cerebral blood flow in cats," Am J Physiol 22:R270-R274 (1987).

Matsui T et al., in an article entitled, "The effects of cervical spinal cord stimulation (cSCS) on experimental stroke," Pacing Clin Electrophysiol 12(4 Pt 2):726-32 (1989).

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989).

Walters BB et al., "Cerebrovascular projections from the sphenopalatine and otic ganglia to the middle cerebral artery of the cat," Stroke 17:488-494 (1986).

Branston NM, "The physiology of the cerebrovascular parasympathetic innervation," British Journal of Neurosurgery 9:319-329 (1995).

Branston NM et al., "Contribution of cerebrovascular parasympathetic and sensory innervation to the short-term control of blood flow in rat cerebral cortex," J Cereb Blood Flow Metab 15(3):525-31 (1995).

Sun Y et al., "Neuronal nitric oxide synthase and ischemia-induced neurogenesis," J Cereb Blood Flow Metab 25(4):485-92 (2005).

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994).

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998).

Jolliet-Riant P, Tillement JP, "Drug transfer across the blood-brain barrier and improvement of brain delivery," Fundam. Clin. Pharmacol., 13, 16-25 (1999).

Syelaz J, Hara H, Pinard E, Mraovitch S, MacKenzie ET, Edvinsson L, "Effects of stimulation of the sphenopalatine ganglion on cortical blood flow in the rat," Journal of Cerebral Blood Flow and Metabolism, 8, 875-878 (1988).

Toda N et al., "Cerebral vasodilation induced by stimulation of the pterygopalatine ganglion and greater petrosal nerve in anesthetized monkeys," Neuroscience 96(2):393-398 (2000).

Varghese et al., "Endoscopic transnasal neurolytic sphenopalatine ganglion block for head and neck cancer pain," J Laryngol Otol 115(5):385-7 (2001).

Roman GC, "Cholinergic dysfunction in vascular dementia," Curr Psychiatry Rep 7(1):18-26 (2005).

Van Gijn J et al., "Subarachnoid haemorrhage: diagnosis, causes and management," Brain 124 249-278 (2001).

Davis SM et al., "Advances in penumbra imaging with MR," Cerebrovasc Dis 17 Suppl 3:23-7 (2004).

Zausinger VS et al., "Neurological impairment in rats after transient middle cerebral artery occlusion: a comparative study under various treatment paradigms," Brain Research 863(1-2):94-105 (2000).

Phan TG et al., "Salvaging the ischaemic penumbra: more than just reperfusion?" Clin Exp Pharmacol Physiol 29(1-2):1-10 (2002).

Zhang ZG et el., "VEGF enhances angiogenesis and promotes blood-brain barrier leakage in the ischemic brain," J Clin Invest 106:829-838 (2000).

Kawamata T et al., "Intracisternal basic fibroblast growth factor (bFGF) enhances behavioral recovery following focal cerebral infarction in the rat," J Cereb Blood Flow Metab 16:542-547 (1996).

Ziche M et al., "Nitric oxide and angiogenesis," J Neurooncol 50:139-148 (2000).

Zhang R et al., "A nitric oxide donor induces neurogenesis and reduces functional deficits after stroke in rats," Ann Neurol 50:602-611 (2001).

de la Torre JC, "Vascular basis of Alzheimer's pathogenesis," Ann NY Acad Sci 977:196-215 (2002).

Hunter AJ et al., "To what extent have functional studies of ischemia in animals been useful in the assessment of potential neuroprotective agents?" Trends Pharmacol Sci 19:59-66 (1998).

Kanner AA et al., "Serum S100beta: a noninvasive marker of blood-brain barrier function and brain lesions," Cancer 97(11):2806-13 (2003).

Tony JFL, "Nitric oxide and the cerebral vascular function," J Biomed Sci 7:16-26 (2000).

Sandgren K et al., "Vasoactive intestinal peptide and nitric oxide promote survival of adult rat myenteric neurons in culture," J Neurosci Res 72(5):595-602 (2003).

Laude K et al., "NO produced by endothelial NO synthase is a mediator of delayed preconditioning-induced endothelial protection," Am J Physiol Heart Circ Physiol 284(6):H2053-60 (2003) (Epub Jan. 9, 2003).

Khan M et al., "S-Nitrosoglutathione reduces inflammation and protects brain against focal cerebral ischemia in a rat model of experimental stroke," J Cereb Blood Flow Metab 25(2):177-92 (2005).

Pluta RM, "Delayed cerebral vasospasm and nitric oxide: review, new hypothesis, and proposed treatment," Pharmacol Ther 105(1):23-56 (2005).

Reis et al., "Electrical Stimulation of Cerebellar Fastigial Nucleus Reduces Ischemic Infarction Elicited by Middle Cerebral Artery Occlusion in Rat," Journal of Cerebral Blood Flow and Metabolism, 11:810-818, 1991.

Nollet et al., "Transcranial magnetic stimulation: review of the technique, basic principles and applications," The Veterinary Journal, 166 (2003) 28-42.

Devoghel JC, "Cluster headache and spenopalatine block," Acta Anaesthesiol Belg., 1981, 32, 101-107, an abstract.

Office Action dated Jul. 16, 2008, which issued during the prosecution of Applicants' U.S. Appl. No. 11/349,020.

Office Action dated Jun. 27, 2008, which issued during the prosecution of Applicants' U.S. Appl. No. 10/518,322.

* cited by examiner

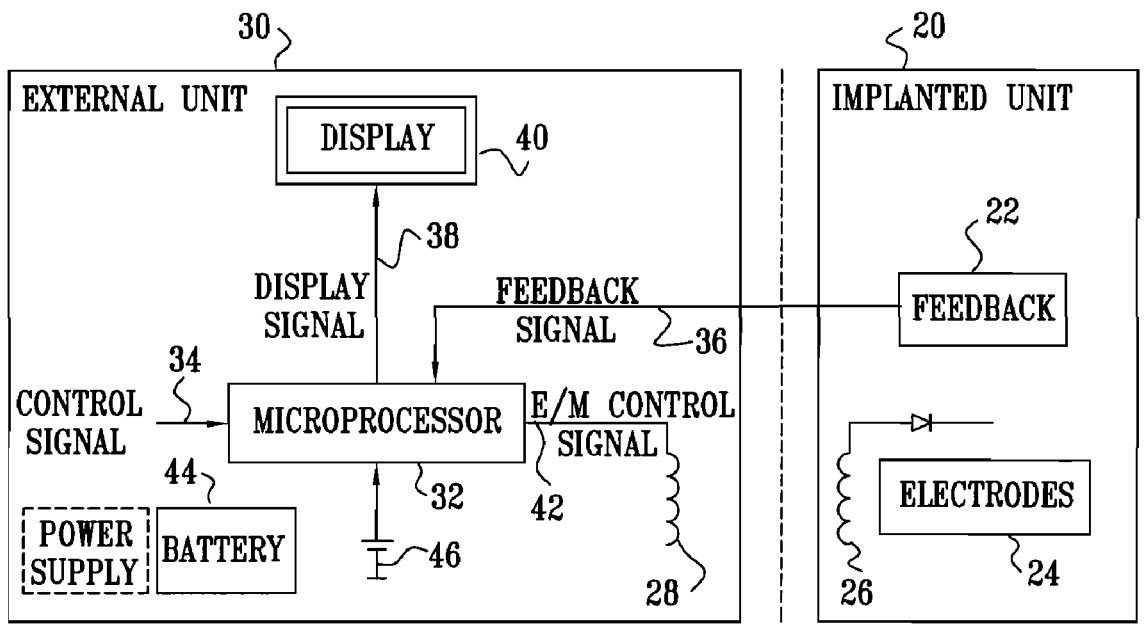
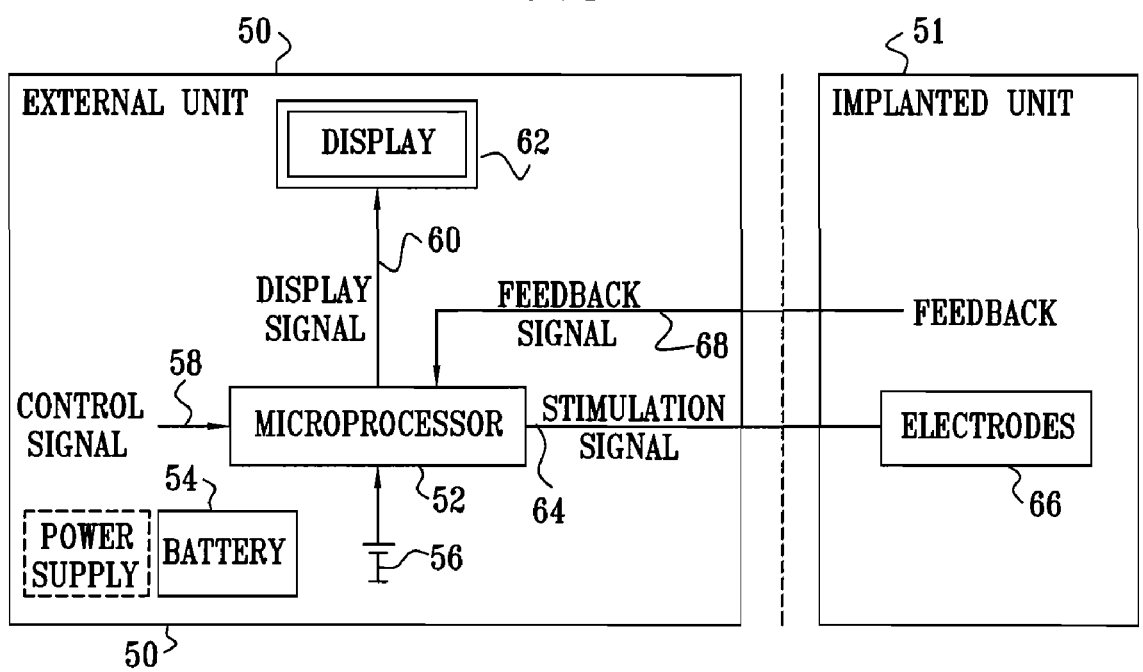

STIMULATION OF THE OTIC GANGLION FOR TREATING MEDICAL CONDITIONS

CROSS-REFERENCES TO RELATED APPLICATIONS

This application is a continuation-in-part of:

(a) U.S. patent application Ser. 10/535,024, filed Dec. 27, 2005, entitled, "Surgical tools and techniques for stimulation," which is the US national stage of International Patent Application PCT/IL03/000966, filed Nov. 13, 2003, entitled, "Surgical tools and techniques for stimulation," which claims the benefit of U.S. Provisional Patent Application 60/426,180, filed Nov. 14, 2002, entitled, "Surgical tools and techniques for stimulation"; and (b) U.S. patent application Ser. No. 10/512,780, filed Jun. 1, 2005, which is the US national stage of International Patent Application PCT/IL03/00338, filed Apr. 25, 2003, which claims the benefit of U.S. Provisional Patent Application 60/376,048, filed Apr. 25, 2002. All three of these applications are entitled, "Methods and apparatus for modifying properties of the BBB and cerebral circulation by using the neuroexcitatory and/or neuroinhibitory effects of odorants on nerves in the head." International Patent Application PCT/IL03/00338 also claims the benefit of U.S. Provisional Patent Application 60/461,232, filed Apr. 8, 2003, entitled, "Treating abnormal conditions of the mind and body by modifying properties of the blood-brain barrier and cephalic blood flow."

All of the above-mentioned applications are assigned to the assignee of the present application and are incorporated herein by reference.

FIELD OF THE INVENTION

The present invention relates generally to medical procedures and electronic devices. More specifically, the invention relates to treating medical conditions using electrical stimulation.

BACKGROUND OF THE INVENTION

The blood-brain barrier (BBB) is a unique feature of the central nervous system (CNS), which isolates the brain from the systemic blood circulation. To maintain the homeostasis of the CNS, the BBB prevents access to the brain for many substances circulating in the blood.

The BBB is formed by a complex cellular system of endothelial cells, astroglia, pericytes, perivascular macrophages, and a basal lamina. Compared to other tissues, brain endothelia have the most intimate cell-to-cell connections: endothelial cells adhere strongly to each other, forming structures specific to the CNS called "tight junctions" or zonula occludens. They involve two opposing plasma membranes, which form a membrane fusion with cytoplasmic densities on either side. These tight junctions prevent cell migration or cell movement between endothelial cells. A continuous uniform basement membrane surrounds the brain capillaries. This basal lamina encloses contractile cells called pericytes, which form an intermittent layer and probably play some role in phagocytosis activity and defense if the BBB is breached. Astrocytic end feet, which cover the brain capillaries, build a continuous sleeve and maintain the integrity of the BBB by the synthesis and secretion of soluble growth factors (e.g., gamma-glutamyl transpeptidase) essential for the endothelial cells to develop their BBB characteristics.

PCT Publication WO 01/85094 and US Patent Application Publications 2004/0015068 and 2004/0210269 to Shalev and Gross, which are assigned to the assignee of the present patent application and are incorporated herein by reference, describe apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 6,853,858 to Shalev, which is assigned to the assignee of the present application and is incorporated herein by reference, describes apparatus for delivering a Non Steroidal Anti-Inflammatory Drug (NSAID) supplied to a body of a subject for delivery to at least a portion of a central nervous system (CNS) of the subject via a systemic blood circulation of the subject. The apparatus includes a stimulator adapted to stimulate at least one site of the subject, so as to cause an increase in passage of the NSAID from the systemic blood circulation across a blood brain barrier (BBB) of the subject to the portion of the CNS, during at least a portion of the time that the NSAID is present in the blood, the site selected from the group consisting of: a sphenopalatine ganglion (SPG), an anterior ethmoidal nerve, a posterior ethmoidal nerve, a communicating branch between an anterior ethmoidal nerve and a retro-orbital branch of an SPG, a communicating branch between a posterior ethmoidal nerve and a retro-orbital branch of an SPG, a greater palatine nerve, a lesser palatine nerve, a sphenopalatine nerve, a communicating branch between a maxillary nerve and an SPG, a nasopalatine nerve, a posterior nasal nerve, an infraorbital nerve, an otic ganglion, an afferent fiber going into the otic ganglion, an efferent fiber going out of the otic ganglion, a vidian nerve, a greater superficial petrosal nerve, and a lesser deep petrosal nerve.

US Patent Application Publication 2004/0220644 to Shalev et al., which is assigned to the assignee of the present application and is incorporated herein by reference, describes a method for treating a subject, including positioning at least one electrode at at least one site of the subject, such as the SPG, for less than about 3 hours, applying an electrical current to the site of the subject, and configuring the current to increase cerebral blood flow (CBF) of the subject, so as to treat a condition of the subject.

US Patent Application Publication 2003/0176898 to Gross et al., which is assigned to the assignee of the present application and is incorporated herein by reference, describes apparatus for treating a condition of an eye of a subject, comprising a stimulator adapted to stimulate at least one site of the subject, such as the SPG, so as to treat the eye condition.

US Patent Application Publication 2005/0159790 to Shalev, which is assigned to the assignee of the present application and is incorporated herein by reference, describes a method for facilitating a diagnosis of a condition of a subject, including applying a current to a site of the subject, such as the SPG, and configuring the current to increase conductance of molecules from brain tissue of the subject through a blood brain barrier (BBB) of the subject into a systemic blood circulation of the subject. The method also includes sensing a quantity of the molecules from a site outside of the brain of the subject, following initiation of application of the current.

US Patent Application Publication 2005/0266099 to Shalev, which is assigned to the assignee of the present application and is incorporated herein by reference, describes a method for modifying a property of a brain of a patient includes presenting an odorant to an air passage of the patient, the odorant having been selected for presentation to the air passage because it is such as to increase conductance of molecules from a systemic blood circulation of the patient through a blood brain barrier (BBB) of the brain into brain tissue of the patient. The molecules are selected from the group consisting of: a pharmacological agent, a therapeutic agent, an endogenous agent, and an agent for facilitating a diagnostic procedure.

PCT Publication WO 04/010923 to Gross et al., which is assigned to the assignee of the present application and is incorporated herein by reference, describes a chemical agent delivery system, including a chemical agent supplied to a body of a subject for delivery to a site in a central nervous system of said subject via blood of said subject; and a stimulator for stimulating parasympathetic fibers associated with the SPG, thereby rendering a blood brain barrier (BBB) of said subject permeable to said chemical agent during at least a portion of the time that said chemical agent is present in said blood.

PCT Publication WO 04/043218 to Gross et al., which is assigned to the assignee of the present application and is incorporated herein by reference, describes apparatus for treating a subject, including (a) a stimulation device, adapted to be implanted in a vicinity of a site selected from the list consisting of: a SPG and a neural tract originating in or leading to the SPG; and (b) a connecting element, coupled to the stimulation device, and adapted to be passed through at least a portion of a greater palatine canal of the subject.

PCT Publication WO 04/045242 to Shalev, which is assigned to the assignee of the present application and is incorporated herein by reference, describes apparatus for treating a condition of an ear of a subject, comprising a stimulator adapted to stimulate at least one site of the subject, such as the SPG, at a level sufficient to treat the ear condition.

PCT Publication WO 05/030025 to Shalev et al., which is assigned to the assignee of the present application and is incorporated herein by reference, describes apparatus for treating a subject, including an elongated generally rigid support element having a length of at least 1.8 cm, and having a distal end. The apparatus also includes one or more electrodes fixed to the support element in a vicinity of the distal end thereof, and configured to be positioned in a vicinity of a site of the subject, such as the SPG, when the support element is inserted into a body of the subject, such that a portion of the support element remains outside of the body. The apparatus further includes a control unit, coupled to the support element, and adapted to drive the electrodes to apply an electrical current to the site, and to configure the current to increase cerebral blood flow (CBF) of the subject, so as to treat a condition of the subject.

U.S. Pat. No. 6,526,318 to Ansarinia and related PCT Publication WO 01/97905 to Ansarinia, which are incorporated herein by reference, describe a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve.

U.S. Pat. No. 6,405,079 to Ansarinia, which is incorporated herein by reference, describes a method for the suppression or prevention of various medical conditions, including pain, movement disorders, autonomic disorders, and neuropsychiatric disorders. The method includes positioning an electrode adjacent to or around a sinus, the dura adjacent a sinus, or falx cerebri, and activating the electrode to apply an electrical signal to the site. In a further embodiment for treating the same conditions, the electrode dispenses a medication solution or analgesic to the site.

U.S. Pat. No. 6,432,986 to Levin and PCT Publication WO 99/03473 to Levin, which are incorporated herein by reference, describe techniques for inhibiting a cerebral neurovascular disorder or a muscular headache. The techniques include intranasally administering a pharmaceutical composition comprising a long-acting local anesthetic.

U.S. Pat. No. 6,491,940 to Levin, US Patent Application 2003/0133877 to Levin, and PCT Publication WO 00/44432 to Levin, which are incorporated herein by reference, describe techniques for inhibiting a cerebral neurovascular disorder or a muscular headache. The techniques include intranasally administering a pharmaceutical composition comprising a long-acting local anesthetic. Apparatus for delivering or applying the composition is also described.

US Patent Application 2001/0004644 to Levin and PCT Publication WO 01/43733 to Levin, which are incorporated herein by reference, describe techniques for inhibiting cephalic inflammation, including meningeal inflammation and cerebral inflammation. The techniques include intranasally administering a long-acting local anesthetic. Apparatus for delivering or applying the composition is also described, including a dorsonasally implanted electronic neural stimulator, such as a transepithelial neural stimulation device.

The following patent application publications, all of which are assigned to the assignee of the present application and are incorporated herein by reference, may be of interest: WO 03/090599, WO 03/105658, WO 04/010923, WO 04/043218, WO 04/044947, WO 04/045242, WO 04/043217, WO 04/043334, WO 05/030025, WO 05/030118, and US 2004/0220644.

The following patents and patent application publications, all of which are incorporated herein by reference, may be of interest: U.S. Pat. No. 5,756,071 to Mattern et al., U.S. Pat. No. 5,752,515 to Jolesz et al., U.S. Pat. Nos. 5,725,471 and 6,086,525 to Davey et al., PCT Publication WO 02/32504 to Zanger et al., US Patent Application Publication 2003/0050527 to Fox et al., U.S. Pat. No. 6,415,184 to Ishikawa et al., PCT Publications WO 03/084591, WO 03/020350, WO 03/000310, WO 02/068031, and WO 02/068029 to Djupesland, and US Patent Application Publication 2003/0079742 to Giroux.

Hotta H et al., in an article entitled, "Effects of stimulating the nucleus basalis of Meynert on blood flow and delayed neuronal death following transient ischemia in rat cerebral cortes," Jap J Phys 52:383-393 (2002), which is incorporated herein by reference, report that stimulation of the nucleus basalis of Meynert (NBM) in the rat was accompanied by vasodilatation and increase in cortical blood flow. They suggest that NBM-originating vasodilative activation can protect the ischemia-induced delayed death of cortical neurons by preventing a blood flow decrease in widespread cortices.

Reis D J et al., in an article entitled, "Electrical stimulation of cerebellar fastigial nucleus reduces ischemic infarction elicited by middle cerebral artery occlusion in rat," J Cereb Blood Flow Metab 11(5):810-8 (1991), which is incorporated herein by reference, report that electrical stimulation of the cerebellar fastigial nucleus (FN) profoundly increases cerebral blood flow via a cholinergic mechanism. Utilizing the rat middle cerebral artery occlusion (MCAO) model, they demonstrated that one hour of electrical stimulation of the FN has the capacity to substantially reduce the infarct size at the rim of the cortex dorsal and ventral to the infarction, and medially within the thalamus and striatum corresponding to the penumbral zone. They conclude that excitation of an intrinsic system in brain represented in the rostral FN has the capacity to substantially reduce an ischemic infarction.

Matsui T et al., in an article entitled, "The effects of cervical spinal cord stimulation (cSCS) on experimental stroke," Pacing Clin Electrophysiol 12(4 Pt 2):726-32 (1989), which is incorporated herein by reference, report that cSCS increases regional cerebral blood flow, and, in a cat middle cerebral artery occlusion model (MCAO), reduced the rate of death within 24 hours after MCAO.

Segher O et al., in an article entitled, "Spinal cord stimulation reducing infract volume in model of focal cerebral ischemia in rats," J Neurosurg 99(1):131-137 (2003), which is incorporated herein by reference, demonstrate that spinal cord stimulation increases cerebral blood flow in rats and significantly reduces stroke volume, suggesting that spinal cord stimulation could be used for treatment and prevention of stroke.

The following references, which are incorporated herein by reference, may be useful:

Delepine L, Aubineau P, "Plasma protein extravasation induced in the rat dura mater by stimulation of the parasympathetic sphenopalatine ganglion," Experimental Neurology, 147, 389-400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822-827 (1993)

Jolliet-Riant P, Tillement J P, "Drug transfer across the blood-brain barrier and improvement of brain delivery," Fundam. Clin. Pharmacol., 13, 16-25 (1999)

Kroll R A, Neuwelt E A, "Outwitting the blood brain barrier for therapeutic purposes: Osmotic opening and other means," Neurosurgery, 42, 1083-1100 (1998)

Syelaz J, Hara H, Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875-878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151-165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383-391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307-315 (1990)

Major A, Silver W, "Odorants presented to the rat nasal cavity increase cortical blood flow," Chem. Senses, 24, 665-669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132-137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307-315 (1984)

Silver W L, "Neural and pharmacological basis for nasal irritation," in Tucker W G, Leaderer B P, Mølhave L, Cain W S (eds), Sources of Indoor Air Contaminants, Ann. NY Acad. Sci., 641, 152-163 (1992)

Silver W, "Chemesthesis: the burning questions," ChemoSense, Vol. 2, 1-2 (1999)

Devoghel J C, "Cluster headache and sphenopalatine block," Acta Anaesthesiol Belg., 32(1):101-7 (1981)

Branston N M, "The physiology of the cerebrovascular parasympathetic innervation," British Journal of Neurosurgery 9:319-329 (1995)

Branston N M et al., "Contribution of cerebrovascular parasympathetic and sensory innervation to the short-term control of blood flow in rat cerebral cortex," J Cereb Blood Flow Metab 15(3):525-31 (1995)

Toda N et al., "Cerebral vasodilation induced by stimulation of the pterygopalatine ganglion and greater petrosal nerve in anesthetized monkeys," Neuroscience 96 (2):393-398 (2000)

Seylaz J et al., "Effect of stimulation of the sphenopalatine ganglion on cortical blood flow in the rat," J Cereb Blood Flow Metab 8(6):875-8 (1988)

Nollet H et al., "Transcranial magnetic stimulation: review of the technique, basic principles and applications," The Veterinary Journal 166:28-42 (2003)

Van Gijn J et al., "Subarachnoid haemorrhage: diagnosis, causes and management," Brain 124:249-278 (2001)

Goadsby P J et al., "Effect of stimulation of trigeminal ganglion on regional cerebral blood flow in cats," Am J Physiol 22:R270-R274 (1987)

Walters B B et al., "Cerebrovascular projections from the sphenopalatine and otic ganglia to the middle cerebral artery of the cat," Stroke 17:488-494 (1986)

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989)

Roth B J et al., "In vitro evaluation of a 4-leaf coil design for magnetic stimulation of peripheral nerve," Electroencephalography and Clinical Neurophysiology 93:68-74 (1994)

Zhang R et al., "A nitric oxide donor induces neurogenesis and reduces functional deficits after stroke in rats," Ann Neurol 50:602-611 (2001)

Ziche M et al., "Nitric oxide and angiogenesis," J Neurooncol 50:139-148 (2000)

Kawamata T et al., "Intracisternal basic fibroblast growth factor (bFGF) enhances behavioral recovery following focal cerebral infarction in the rat," J Cereb Blood Flow Metab 16:542-547 (1996)

Zhang Z G et el., "VEGF enhances angiogenesis and promotes blood-brain barrier leakage in the ischemic brain," J Clin Invest 106:829-838 (2000)

Sun Y et al., "Neuronal nitric oxide synthase and ischemia-induced neurogenesis," J Cereb Blood Flow Metab 25(4):485-92 (2005)

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994)

Beridze M et al., "Effect of nitric oxide initial blood levels on erythrocyte aggregability during 12 hours from ischemic stroke onset," Clin Hemorheol Microcirc 30(3-4):403-6 (2004)

Davis S M et al., "Advances in penumbra imaging with MR," Cerebrovasc Dis 17 Suppl 3:23-7 (2004)

Phan T G et al., "Salvaging the ischaemic penumbra: more than just reperfusion?" Clin Exp Pharmacol Physiol 29(1-2):1-10 (2002)

Gressens P et al., "Neuroprotection of the developing brain by systemic administration of vasoactive intestinal peptide derivatives," J Pharmacol Exp Ther 288 (3):1207-13 (1999)

Zhang R et al., "Nitric oxide enhances angiogenesis via the synthesis of vascular endothelial growth factor and cGMP after stroke in the rat," Circ Res 21;92(3):308-13 (2003)

de la Torre J C, "Vascular basis of Alzheimer's pathogenesis," Ann NY Acad Sci 977:196-215 (2002)

Roman G C, "Cholinergic dysfunction in vascular dementia," Curr Psychiatry Rep 7(1):18-26 (2005)

Tony J F L, "Nitric oxide and the cerebral vascular function," J Biomed Sci 7:16-26 (2000)

Pluta R M, "Delayed cerebral vasospasm and nitric oxide: review, new hypothesis, and proposed treatment," Pharmacol Ther 105(1):23-56 (2005)

Sandgren K et al., "Vasoactive intestinal peptide and nitric oxide promote survival of adult rat myenteric neurons in culture," J Neurosci Res 72(5):595-602 (2003)

Laude K et al., "NO produced by endothelial NO synthase is a mediator of delayed preconditioning-induced endothelial protection," Am J Physiol Heart Circ Physiol 284(6):H2053-60 (2003) (Epub Jan. 9, 2003)

Khan M et al., "S-Nitrosoglutathione reduces inflammation and protects brain against focal cerebral ischemia in a rat model of experimental stroke," J Cereb Blood Flow Metab 25(2):177-92 (2005)

Molloy J et al., "S-nitrosoglutathione reduces the rate of embolization in humans," Circulation 98(14):1372-5 (1998)

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998)

Zausinger V S et al., "Neurological impairment in rats after transient middle cerebral artery occlusion: a comparative study under various treatment paradigms," Brain Research 863(1-2):94-105 (2000)

Hunter A J et al., "To what extent have functional studies of ischemia in animals been useful in the assessment of potential neuroprotective agents?" Trends Pharmacol Sci 19:59-66 (1998)

Varghese et al., "Endoscopic transnasal neurolytic sphenopalatine ganglion block for head and neck cancer pain," J Laryngol Otol 115(5):385-7 (2001)

Kanner A A et al., "Serum S100beta: a noninvasive marker of blood-brain barrier function and brain lesions," Cancer 97(11):2806-13 (2003)

SUMMARY OF THE INVENTION

In some embodiments of the present invention, apparatus for treating a condition of a subject comprises one or more electrodes coupled to a stimulator. The electrodes are configured to be applied to an "otic-ganglion site" of the subject selected from the group consisting of: an otic ganglion, associated neural tracts of the otic ganglion, an afferent fiber going into the otic ganglion, and an efferent fiber going out of the otic ganglion. The stimulator is configured to drive the electrodes to apply a current to the otic-ganglion site, and to configure the current to control and/or modify otic-ganglion-related behavior, e.g., in order to induce changes in cerebral blood flow (CBF) and/or to modulate permeability of the blood-brain-barrier (BBB). These embodiments may be used in many medical applications, such as, by way of illustration and not limitation, (a) the treatment of cerebrovascular disorders such as stroke, (b) the treatment of migraine headaches, (c) the facilitation of drug transport across the BBB, and/or (d) the facilitation of extraction of analytes from the brain.

Whereas the SPG and SPG-related sites, as described in above-mentioned PCT Publication WO 01/85094, are believed to play a role in innervating most of the more anterior cephalic circulation, otic-ganglion sites are believed to play a dominant role in controlling the properties of the more posterior cephalic circulation.

The stimulator is typically configured to configure the current to activate (i.e., excite) the otic-ganglion site. Alternatively, for some applications, the stimulator is configured to configure the current to block (i.e., inhibit) activity of the otic-ganglion site.

In some embodiments of the present invention, a method and apparatus are provided to enhance delivery of therapeutic molecules across the BBB by stimulation of the otic-ganglion site. The apparatus typically stimulates the parasympathetic nerve fibers of the otic-ganglion site, thereby causing cerebral arteries walls to become more permeable to large molecules. In this manner, the movement of large pharmaceutical molecules from within blood vessels to the cerebral tissue is substantially increased. Typically, therefore, this method can serve as a neurological drug delivery facilitator, without the sacrifices in molecular weight required by techniques of the prior art. In general, it is believed that substantially all pharmacological treatments aimed at cerebral cells for neurological and psychiatric disorders are amenable for use with these embodiments of the present invention. In particular, these embodiments may be adapted for use in the treatment of disorders such as brain tumors, epilepsy, Parkinson's disease, Alzheimer's disease, multiple sclerosis, schizophrenia, depression, stress, anxiety, and any other CNS disorders that are directly or indirectly affected by changes in cerebral blood flow or by BBB permeability changes.

Advantageously (and even in the absence of BBB permeability changes), patients with these and other disorders are generally helped by the vasodilation secondary to stimulation of the otic-ganglion site, and the resultant improvement in oxygen supply to neurons and other tissue. For some applications, this treatment is given on a long-term basis, e.g., in the chronic treatment of Alzheimer's patients. For other applications, the treatment is performed on a short-term basis, e.g., to minimize the damage following an acute stroke event and initiate neuronal and therefore functional rehabilitation.

For most applications, it is expected that the electrode(s) will remain implanted for a period of at least about one month; in some other applications, the period of implantation may be less than one week. Implantation may be performed by microsurgical techniques. For some applications, electrical leads are employed to deliver the electrical stimulating signal from the generator to the electrode(s), and thence a stimulus from the electrode(s) to the tissue, while for other applications, wireless delivery is used. Further, for some applications, the stimulus generator is sufficiently small as to be implantable, e.g., in the roof of the mouth or in a nasal cavity of the patient. The size of the stimulator is principally a function of battery size, and in turn, the energy required to be delivered to the electrode(s) and the period of time of such delivery.

In another aspect of the present invention, to be discussed in greater detail below, the need for a battery is eliminated by use of a technique for energizing the stimulus generator from a location external to the patient, without an adverse effect on the patient.

The apparatus may include a biosensor to measure or detect a designated physiological parameter of the patient and to generate a signal responsive thereto as an indication of satisfactory implantation or operation of the device and/or for feedback to control the operation of the stimulus generator.

In some embodiments of the present invention, a stimulus device produces a stimulus in the form of one of an electrical signal, an electromagnetic field, magnetic induction, a mechanical stimuli, a chemical agent, an odorant, an acoustic signal, an optical signal, or a combination of two or more thereof.

In some embodiments of the present invention, an otic-ganglion site is stimulated in order to increase passage through the BBB of a molecular substance from systemic cardiovascular circulation into the central nervous system (CNS), the molecular substance selected from a group consisting of a therapeutic drug, a pharmaceutical, a chemical agent, a growth factor, an enzyme, a protein in general, a viral vector and a gene factor, the selected molecular substance having been introduced into the patient's systemic blood circulation to therapeutically treat the diagnosed disease or disorder. In some instances, an otic-ganglion site is stimulated to inhibit passage through the BBB of a molecular substance from the central nervous system (CNS) into the patient's systemic cardiovascular circulation. In other instances, an otic-ganglion site is stimulated to inhibit passage through the BBB of a molecular substance from the systemic cardiovascular circulation into the patient's central nervous system (CNS). In many instances, an otic-ganglion site stimulated to increase CBF.

In some embodiments of the present invention, apparatus is provided for treating a diagnosed disease or disorder of or related to activity of a patient's brain from among primary brain tumors, metastatic brain tumors, dementia, AD, alcohol or chemical addiction or abuse, ALS, stroke, head injury, brain injury, Huntington's disease, MS, depression, cerebral palsy, Parkinson's disease, schizophrenia, epilepsy, migraine, stress, anxiety, obesity, eye- and ear-related or other CNS disorders. The apparatus includes a device for producing a stimulus having parameters selected to modify permeability of the patient's blood-brain barrier (BBB) when the stimulus is delivered to an otic-ganglion site, and a delivery system adapted for operative coupling to the stimulus device and to the otic-ganglion site to introduce the stimulus produced by the stimulus device to the otic-ganglion site so as to module CBF and/or adjust permeability of the BBB to apply therapeutic treatment of the diagnosed disease or disorder.

There is therefore provided, in accordance with an embodiment of the present invention, apparatus including:

one or more electrodes, adapted to be applied to an otic-ganglion site of a patient selected from the group consisting of: an otic ganglion, an associated neural tract of the otic ganglion, an afferent fiber going into the otic ganglion, and an efferent fiber going out of the otic ganglion; and a stimulator, configured to:

drive the one or more electrodes to apply a current to the otic-ganglion site, and configure the current to activate the otic-ganglion site sufficiently to induce at least one effect selected from the group consisting of: a change in cerebral blood flow (CBF) of the patient, and a change in permeability of a blood-brain-barrier (BBB) of the patient.

In an embodiment, the stimulator is configured to configure the current to activate the otic-ganglion site sufficiently to induce an increase in the CBF. For some applications, the stimulator is configured to configure the current to activate the otic-ganglion site sufficiently to treat stroke of the patient, by inducing the increase in the CBF. For some applications, the stimulator is configured to configure the current to activate the otic-ganglion site sufficiently to treat a condition of the patient, by inducing the increase in the CBF, the condition selected from the group consisting of: depression, and anxiety. Alternatively, the stimulator is configured to configure the current to activate the otic-ganglion site sufficiently to treat a condition of the patient, by inducing a change in the CBF, the condition selected from the group consisting of: depression, and anxiety.

In an embodiment, the stimulator is configured to configure the current to activate the otic-ganglion site sufficiently to induce an increase in BBB permeability. For some applications, the stimulator is configured to configure the current to activate the otic-ganglion site sufficiently to facilitate drug transport across the BBB, by inducing the increase in BBB permeability.

For some applications, the stimulator is configured to configure the current to control properties of posterior cephalic circulation.

For some applications, the stimulator is configured to drive the one or more electrodes to apply the current on a long-term basis.

In an embodiment, the otic-ganglion site includes the otic ganglion, the one or more electrodes are adapted to be applied to the otic ganglion, and the stimulator is configured to drive the one or more electrodes to apply the current to the otic ganglion. Alternatively or additionally, the otic-ganglion site includes the associated neural tract of the otic ganglion, the one or more electrodes are adapted to be applied to the associated neural tract of the otic ganglion, and the stimulator is configured to drive the one or more electrodes to apply the current to the associated neural tract of the otic ganglion. Further alternatively or additionally, the otic-ganglion site is selected from the group consisting of: the afferent fiber going into the otic ganglion, and the efferent fiber going out of the otic ganglion, the one or more electrodes are adapted to be applied to the selected site, and the stimulator is configured to drive the one or more electrodes to apply the current to the selected site.

For some applications, the stimulator is configured to be implanted in a body of the patient.

For some applications, the stimulator includes circuitry, which includes: an implantable unit, configured to be implanted in a body of the patient, the implantable unit including an implantable unit coupler; and an external unit, including an external unit coupler configured to be wirelessly coupled to the implantable unit coupler, the external unit configured to convey a control signal from the external unit coupler to the implantable unit coupler, which signal drives the implantable unit to drive the electrodes to apply the current to the site.

For some applications, the one or more electrodes are adapted for a period of implantation in the patient of greater than about one month. Alternatively, for some applications, the one or more electrodes are adapted for a period of implantation in the patient of less than one week.

For some applications, the stimulator is configured to drive the one or more electrodes by wireless communication from a position external to the patient.

In an embodiment, the stimulator is configured to configure the current to activate the otic-ganglion site sufficiently to treat a condition of the patient selected from the group consisting of: a brain tumor, epilepsy, Parkinson's disease, Alzheimer's disease, multiple sclerosis, schizophrenia, and stress.

There is further provided, in accordance with an embodiment of the present invention, a method including:

selecting an otic-ganglion site of a patient from the group consisting of: an otic ganglion, an associated neural tract of the otic ganglion, an afferent fiber going into the otic ganglion, and an efferent fiber going out of the otic ganglion; and applying a current to the otic-ganglion site, and configuring the current to activate the site sufficiently to induce at least one effect selected from the group consisting of: a change in cerebral blood flow (CBF) of the patient, and a change in permeability of a blood-brain-barrier (BBB) of the patient.

For some applications, the method includes identifying that the patient may benefit from the at least one effect, and applying the current includes applying the current responsively to the identifying.

The present invention will be more fully understood from the following detailed description of the embodiments thereof, taken together with the drawings in which:

BRIEF DESCRIPTION OF THE DRAWINGS

FIG. 3 is a schematic block diagram illustrating circuitry comprising an implanted unit and an external unit, for use with the stimulator of FIG. 1, in accordance with an embodiment of the present invention;

FIG. 4 is a schematic block diagram of circuitry for use, for example, in conjunction with the control unit of FIG. 2, in accordance with an embodiment of the present invention;

DETAILED DESCRIPTION OF EMBODIMENTS

Figure 1:
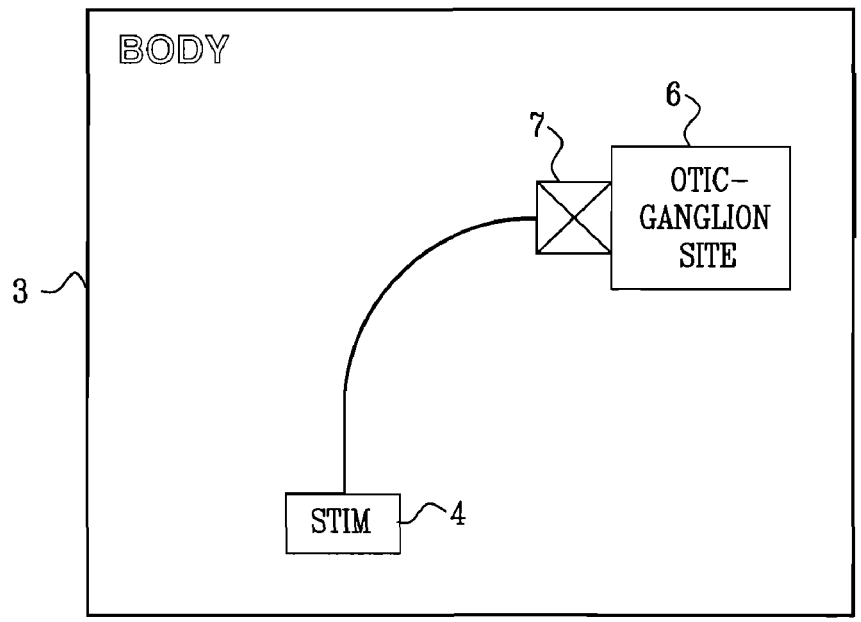
FIG. 1 is a schematic illustration of a fully-implantable stimulator, for stimulation of an otic-ganglion site of a patient, in accordance with an embodiment of the present invention.

FIG. 1 is a schematic illustration of a fully-implantable stimulator 4, for stimulation of an otic-ganglion site 6 of a body 3 of a patient, in accordance with an embodiment of the present invention. As used in the present application, an "otic-ganglion site" is selected from the group consisting of: an otic ganglion, associated neural tracts of the otic ganglion, an afferent fiber going into the otic ganglion, and an efferent fiber going out of the otic ganglion. Typically, one or more relatively short electrodes 7 extend from stimulator 4 to contact or to be in a vicinity of otic-ganglion site 6 or of nerves innervating otic-ganglion site 6.

For some applications, stimulator 4 is implanted on top of the bony palate, in the bottom of the nasal cavity. Alternatively or additionally, the stimulator is implanted at the lower side of the bony palate, at the top of the oral cavity. Further alternatively or additionally, the stimulator may be directly attached to the otic-ganglion site.

For some applications, a process for placing stimulator 4 is facilitated by fluoroscopy, x-ray guidance, fine endoscopic surgery (FES) techniques or by any other effective guidance method known in the art, or by combinations of the aforementioned. Typically, the ambient temperature and/or cerebral blood flow is measured concurrently with insertion. The cerebral blood flow may be measured with, for example, a laser Doppler unit positioned at the patient's forehead or transcranial Doppler measurements. Verification of proper implantation of the electrodes onto the appropriate neural structure may be performed by activating the device, and generally simultaneously monitoring cerebral blood flow.

The passage of certain molecules from cerebral blood vessels into the brain is hindered by the BBB. The endothelium of the capillaries, the plasma membrane of the blood vessels, and the foot processes of the astrocytes all impede uptake by the brain of the molecules. The BBB generally allows only small molecules (e.g., hydrophilic molecules of molecular weight less than about 200 Da, and lipophilic molecules of less than about 500 Da) to pass from the circulation into the brain.

In accordance with an embodiment of the present invention, parasympathetic activation induced by current from stimulator 4 overcomes the resistance to trans-BBB molecular movement generated by the endothelium of the cerebral capillaries and the plasma membrane. For some applications, therefore, stimulator 4 may be used to transiently remove a substantial obstacle to the passage of drugs from the blood to the brain. For example, the stimulator may cyclically apply current for about two minutes, and subsequently have a rest period of between about 1 and 20 minutes.

It is hypothesized that two neurotransmitters play an important role in this change in properties of the BBB—vasoactive intestinal polypeptide (VIP) and nitric oxide (NO). (Acetylcholine may also be involved.) VIP is a short peptide, and NO is a gaseous molecule. VIP is believed to be a major factor in facilitating plasma protein extravasation (PPE), while NO is responsible for vasodilation. For some applications, stimulator 4 is adapted to vary parameters of the current applied to the otic-ganglion site, as appropriate, in order to selectively influence the activity of one or both of these neurotransmitters. For example, stimulation of the parasympathetic nerve at different frequencies can induce differential secretion—low frequencies cause secretion of NO, while high frequencies (e.g., above about 10 Hz) cause secretion of peptides (VIP).

For other applications, a constant level DC signal, or a slowly varying voltage ramp is applied, in order to block parasympathetic neural activity in affected tissue. Alternatively, similar results can be obtained by stimulating at a rate higher than about 10 Hz, because this tends to exhaust neurotransmitters. Thus, stimulator 4 may be configured to induce parasympathetic electrical block, in order to cause vasoconstriction by mimicking the overall effect of chemical block on the otic-ganglion site. This vasoconstrictive effect may be used, for example, to controllably prevent or reverse the formation of migraine headaches.

Figure 2:
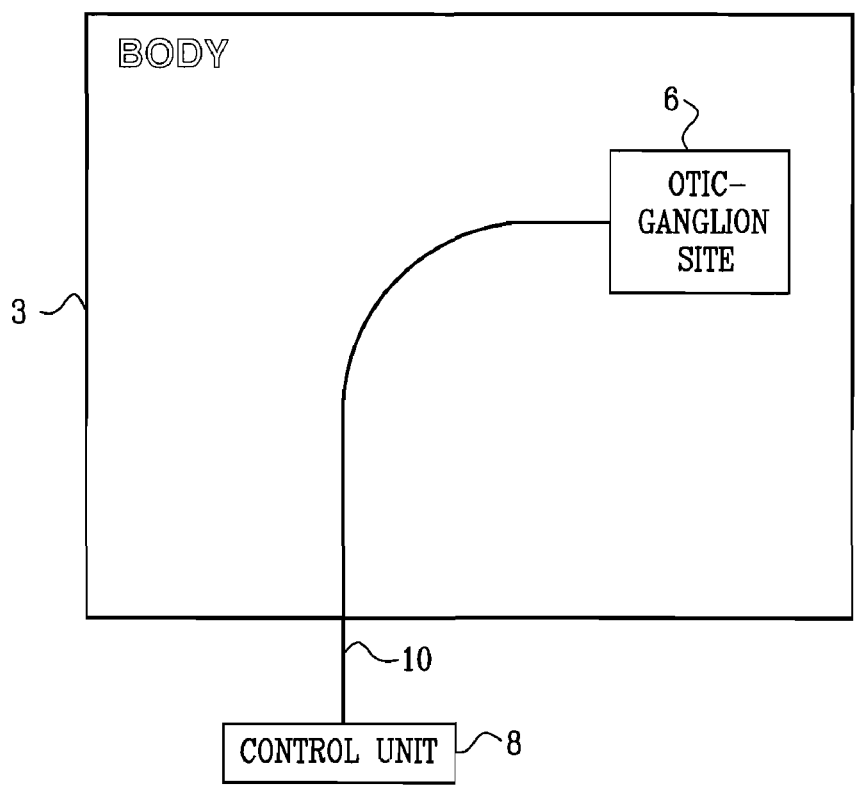
FIG. 2 is a schematic illustration of a stimulator control unit positioned external to a patient, in accordance with an embodiment of the present invention.

FIG. 2 is a schematic illustration of a stimulator control unit 8 positioned external to body 3 of a patient, in accordance with an embodiment of the present invention. At least one flexible electrode 10 typically extends from control unit 8 to a position within body 3 that is adjacent to otic-ganglion site 6.

It is to be understood that electrodes 7 (FIG. 1) and 10 may each comprise one or more electrodes, e.g., two electrodes, or an array of microelectrodes. For applications in which stimulator 4 comprises a metal housing that can function as an electrode, then typically one electrode 7 is used, operating in a monopolar mode. Regardless of the total number of electrodes in use, typically only a single or a double electrode extends to otic-ganglion site 6. Other electrodes 7 or 10 or a metal housing of stimulator 4 are typically temporarily or permanently implanted in contact with other parts of body 3.

Each of electrodes 7 and/or 10 typically comprises a suitable conductive material, for example, a physiologically-acceptable material such as silver, iridium, platinum, a platinum iridium alloy, titanium, nitinol, or a nickel-chrome alloy. For some applications, one or more of the electrodes have lengths ranging from about 1 to 5 mm, and diameters ranging from about 50 to 100 microns. Each electrode is typically insulated with a physiologically-acceptable material such as polyethylene, polyurethane, or a co-polymer of either of these. The electrodes are typically spiral in shape, for better contact, and may have a hook shaped distal end for hooking into or near the otic-ganglion site. Alternatively or additionally, the electrodes may comprise simple wire electrodes, spring-loaded "crocodile" electrodes, or adhesive probes, as appropriate.

In an embodiment of the invention, each one of electrodes 7 and/or 10 comprises a substantially smooth surface, except that the distal end of each such electrode is configured or treated to have a large surface area. For example, the distal tip may be porous platinized. Alternatively or additionally, at least the tip of electrode 7 or 10, and/or a metal housing of stimulator 4 includes a coating comprising an anti-inflammatory drug, such as beclomethasone sodium phosphate or beclomethasone phosphate. Alternatively, such an anti-inflammatory drug is injected or otherwise applied.

FIG. 3 is a schematic block diagram illustrating circuitry comprising an implanted unit 20 and an external unit 30, for use with stimulator 4 (FIG. 1), in accordance with an embodiment of the present invention. Implanted unit 20 typically comprises a feedback block 22 and one or more sensing or signal application electrodes 24. Implanted unit 20 typically also comprises an electromagnetic coupler 26, which receives power and/or sends or receives data signals to or from an electromagnetic coupler 28 in external unit 30.

External unit 30 typically comprises a microprocessor 32 which receives an external control signal 34 (e.g., from a physician or from the patient), and a feedback signal 36 from feedback block 22. Control signal 34 may include, for example, operational parameters such as a schedule of operation, patient parameters such as the patient's weight, or signal parameters, such as desired frequencies or amplitudes of a signal to be applied to the otic-ganglion site. If appropriate, control signal 34 can comprise an emergency override signal, entered by the patient or a healthcare provider to terminate stimulation or to modify it in accordance with a predetermined program. Microprocessor 32, in turn, typically processes control signal 34 and feedback signal 36 so as to determine one or more parameters of the electric current to be applied through electrodes 24. Responsive to this determination, microprocessor 32 typically generates an electromagnetic control signal 42 that is conveyed by electromagnetic coupler 28 to electromagnetic coupler 26. Control signal 42 typically corresponds to a desired current or voltage to be applied by electrodes 24 to otic-ganglion site 6, and, in an embodiment, inductively drives the electrodes. The configuration of couplers 26 and 28 and/or other circuitry in units 20 or 30 may determine the intensity, frequency, shape, monophasic or biphasic mode, or DC offset of the signal (e.g., a series of pulses) applied to designated tissue.

Power for microprocessor 32 is typically supplied by a battery 44 or, optionally, another DC power supply. Grounding is provided by battery 44 or a separate ground 46. If appropriate, microprocessor 32 generates a display signal 38 that drives a display block 40 of external unit 30. Typically, but not necessarily, the display is activated to show feedback data generated by feedback block 22, or to provide a user interface for the external unit.

Implanted unit 20 is typically packaged in a case made of titanium, platinum or an epoxy or other suitable biocompatible material. Should the case be made of metal, then the case may serve as a ground electrode and, therefore, stimulation typically is performed in a monopolar mode. Alternatively, should the case be made of biocompatible plastic material, two electrodes 24 are typically driven to apply current to the otic-ganglion site.

For some applications, the waveform applied by one or more of electrodes 24 to designated tissue (e.g., the otic-ganglion site) comprises a waveform with an exponential decay, a ramp up or down, a square wave, a sinusoid, a saw tooth, a DC component, or any other shape known in the art to be suitable for application to tissue. Alternatively or additionally, the waveform comprises one or more bursts of short shaped or square pulses—each pulse typically less than about 1 ms in duration. Generally, appropriate waveforms and parameters thereof are determined during an initial test period of external unit 30 and implanted unit 20. For some applications, the waveform is dynamically updated according to measured physiological parameters, measured during a period in which unit 20 is stimulating the otic-ganglion site, and/or during a non-activation (i.e., standby) period.

In the case of migraine treatment, the waveform may take the form of a slowly varying shape, such as a slow saw tooth, or a constant DC level, intended to block outgoing parasympathetic messaging.

FIG. 4 is a schematic block diagram of circuitry for use, for example, in conjunction with control unit 8 (FIG. 2), in accordance with an embodiment of the present invention. An external unit 50 comprises a microprocessor 52 supplied by a battery 54 or another DC power source. Grounding may be provided by battery 54 or by a separate ground 56. Microprocessor 52 typically receives control and feedback signals 58 and 68 (analogous to signal 34 and 36 described hereinabove), and generates responsive thereto a stimulation signal 64 conveyed by one or more electrodes 66 to the otic-ganglion site or other tissue. Typically, but not necessarily, feedback signal 68 comprises electrical feedback measured by one or more of electrodes 66 and/or feedback from other sensors on or in the patient's brain or elsewhere coupled to the patient's body. If appropriate, microprocessor 52 generates a display signal 60 which drives a display block 62 to output relevant data to the patient or the patient's physician. Typically, some or all of electrodes 66 are temporarily implanted in the patient (e.g., following a stroke), and are directly driven by wires connecting the external unit to the implanted unit.

Figure 5A:
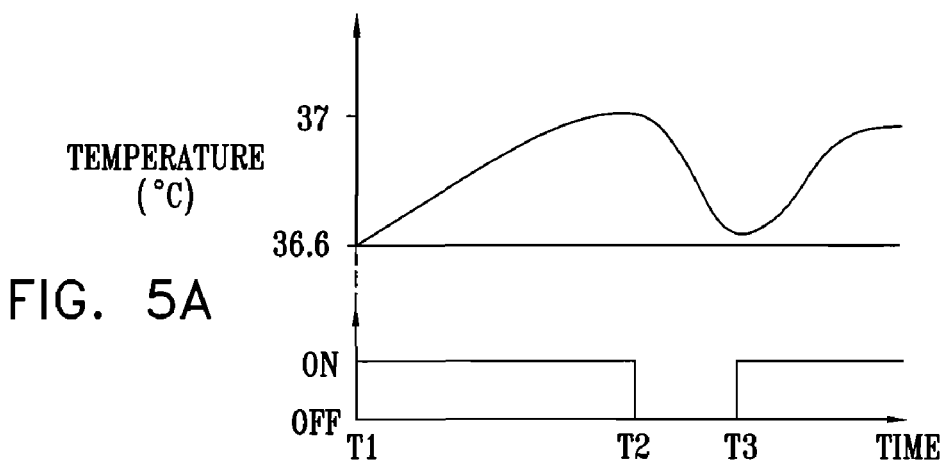
FIGS. 5A-B and 6 are graphs schematically illustrating modes of operation of one or more of the devices shown in FIGS. 1-4, in accordance with respective embodiments of the present invention.

FIG. 5A is a graph schematically illustrating a mode of operation of one or more of the devices shown in FIGS. 1-4, in accordance with an embodiment of the present invention. Typically, the effect of the applied stimulation is monitored by means of a temperature transducer at the otic-ganglion site or elsewhere in the head, e.g., in the nasal cavity. As shown in FIG. 5A for a step (ON/OFF) mode of stimulation, stimulation of the otic-ganglion site or related tissue is initiated at a time T1, and this is reflected by a measurable rise in temperature (due to increased blood flow). Once the temperature rises to a predetermined or dynamically-varying threshold (e.g., 37° C.), stimulation is terminated (time T2), responsive to which the temperature falls. As appropriate, when the temperature drops to a designated or dynamically-determined point, the stimulation is reinitiated (time T3). Typically, suitable temperatures or other physiological parameters are determined for each patient so as to provide the optimal treatment. If appropriate, control instructions may also be received from the patient, e.g., to initiate stimulation upon the onset of a migraine headache.

Figure 5B:
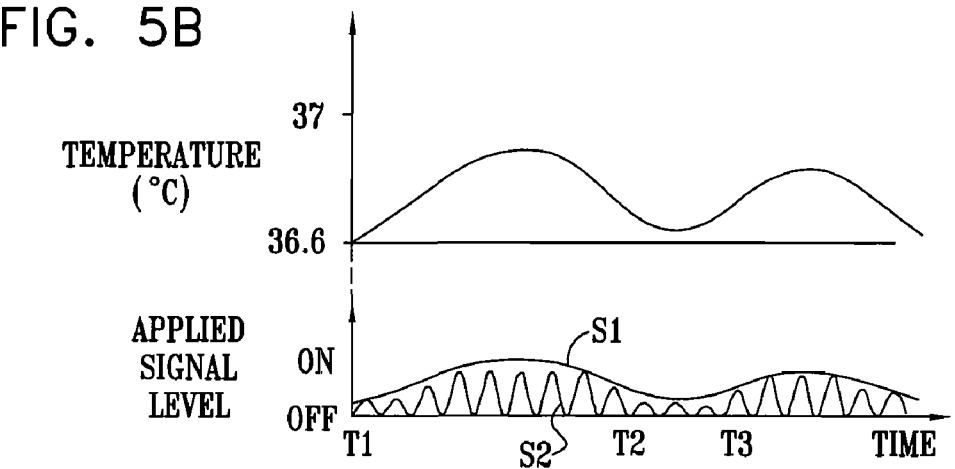

FIG. 5B is a graph schematically illustrating a mode of operation of one or more of the devices shown in FIGS. 1-4, in accordance with another embodiment of the present invention. In this embodiment, the amplitude of the waveform applied to the otic-ganglion site is varied among a continuous set of values (S1), or a discrete set of values (S2), responsive to the measured temperature, in order to achieve the desired performance. It will be appreciated that other feedback parameters measured in the head (e.g., intracranial pressure and/or cerebral blood flow), as well as measured systemic parameters (e.g., heart rate) and subjective patient inputs (e.g., migraine pain=3/5) may be used in conjunction with or separately from temperature measurements, in order to achieve generally optimal performance of the implanted apparatus.

Figure 6:
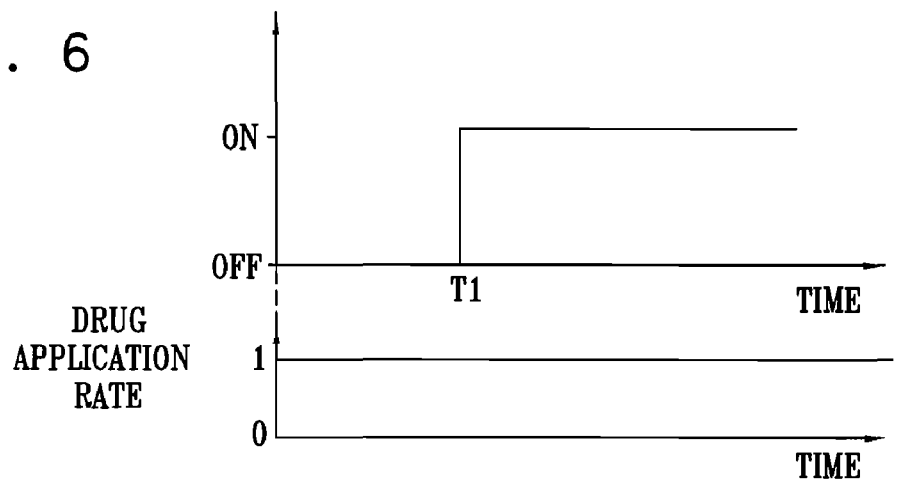

FIG. 6 is a graph schematically illustrating a mode of operation of one or more of the devices shown in FIGS. 1-4, in accordance with an embodiment of the present invention. In this embodiment, a drug is administered to the patient at a constant rate, e.g., intravenously, prior to the initiation of stimulation of the otic-ganglion site at time T1. Advantageously, this prior generation of heightened concentrations of the drug in the blood tends to provide relatively rapid transfer of the drug across the BBB and into the brain, without unnecessarily prolonging the enhanced permeability of the BBB while waiting for the blood concentration of the drug to reach an appropriate level. Alternatively, for some applications it is desirable to give a single injection of a bolus of the drug shortly before or after initiation of stimulation of the otic-ganglion site. Typically, combined administration and stimulation schedules are determined by the patient's physician based on the biochemical properties of each drug targeted at the brain.

Figure 7:
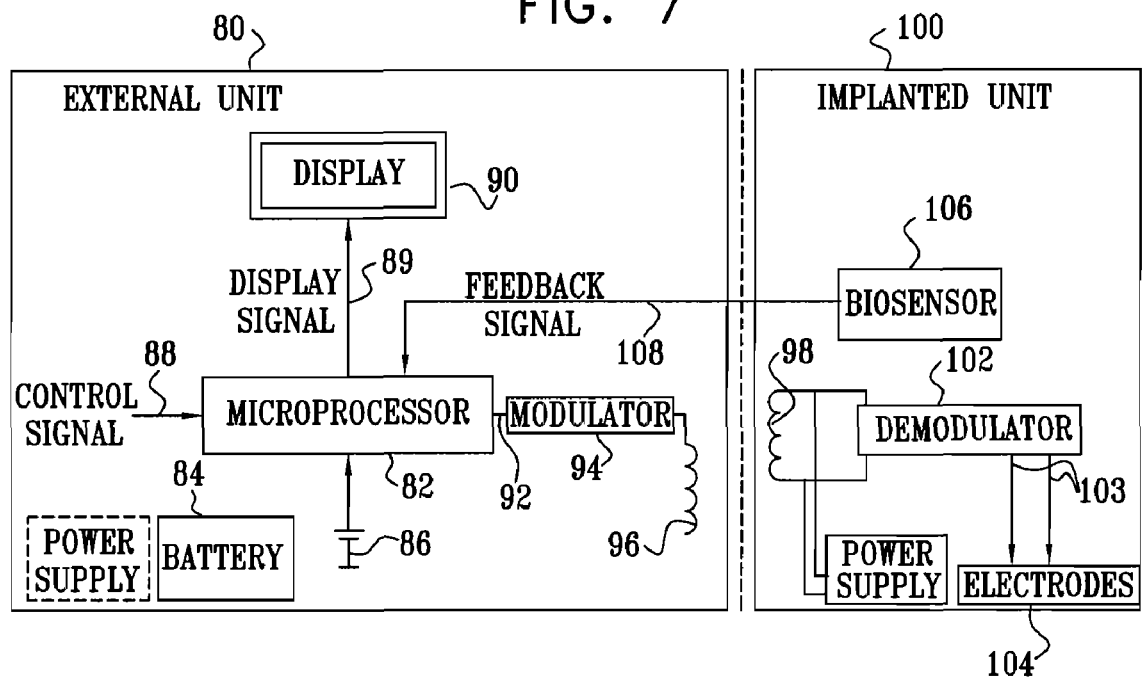
FIG. 7 is a schematic block diagram showing circuitry for parasympathetic stimulation, which is particularly useful in combination with the embodiment shown in FIG. 1, in accordance with an embodiment of the present invention.

FIG. 7 is a schematic block diagram showing circuitry for parasympathetic stimulation, which is particularly useful in combination with the embodiment shown in FIG. 1, in accordance with an embodiment of the present invention. An external unit 80 typically comprises a microprocessor 82 that is powered by a battery 84 and/or an AC power source. Microprocessor 82 is grounded through battery 84 or through an optional ground 86.

In a typical mode of operation, an external control signal 88 is input to microprocessor 82, along with a feedback signal 108 from one or more biosensors 106, which are typically disposed in a vicinity of an implanted unit 100 or elsewhere on or in the patient's body. Responsive to signals 88 and 108, microprocessor 82 typically generates a display signal 89 which drives a display 90, as described hereinabove. In addition, microprocessor 82 typically processes external control signal 88 and feedback signal 108, to determine parameters of an output signal 92, which is modulated by a modulator 94. The output therefrom typically drives a current through an electromagnetic coupler 96, which inductively drives an electromagnetic coupler 98 of implanted unit 100. A demodulator 102, coupled to electromagnetic coupler 98, in turn, generates a signal 103 which drives at least one electrode 104 to apply current to the otic-ganglion site or to other tissue, as appropriate.

Typically, biosensor 106 comprises implantable or external medical apparatus including, for example, one or more of the following:
 a blood flow sensor,
 a temperature sensor,
 a chemical sensor,
 an ultrasound sensor,
 transcranial Doppler (TCD) apparatus,
 laser-Doppler apparatus,
 a systemic or intracranial blood pressure sensor (e.g., comprising a piezoelectric crystal fixed to a major cerebral blood vessel, capable of detecting a sudden blood pressure increase indicative of a clot),
 a kinetics sensor, comprising, for example, an acceleration, velocity, or level sensor (e.g., a mercury switch), for indicating body dispositions such as a sudden change in body attitude (as in collapsing),
 an electroencephalographic (EEG) sensor comprising EEG electrodes attached to, or implanted in, the patients head, for indicating changes in neurological patterns, such as symptoms of stroke or migraine,
 a blood vessel clot detector (e.g., as described hereinbelow with reference to FIG. 13), or
 other monitors of physiological quantities suitable for carrying out the objects of this or other embodiments of the present invention.

Figure 8:
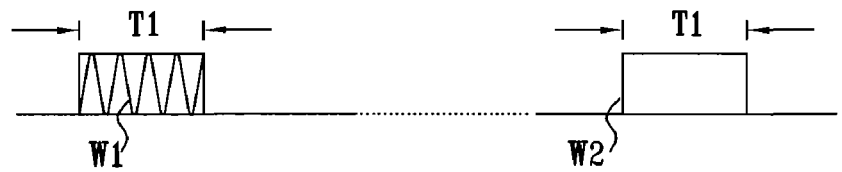
FIG. 8 is a schematic illustration showing operational modes of a modulator and/or a demodulator, in accordance with an embodiment of the present invention.

FIG. 8 is a schematic illustration showing operational modes of modulator 94 and/or demodulator 102, in accordance with an embodiment of the present invention. The amplitude and frequency of signal 92 in FIG. 7 can have certain values, as represented in the left graph; however, the amplitude and frequency are modulated so that signal 103 has different characteristics.

Figure 9:
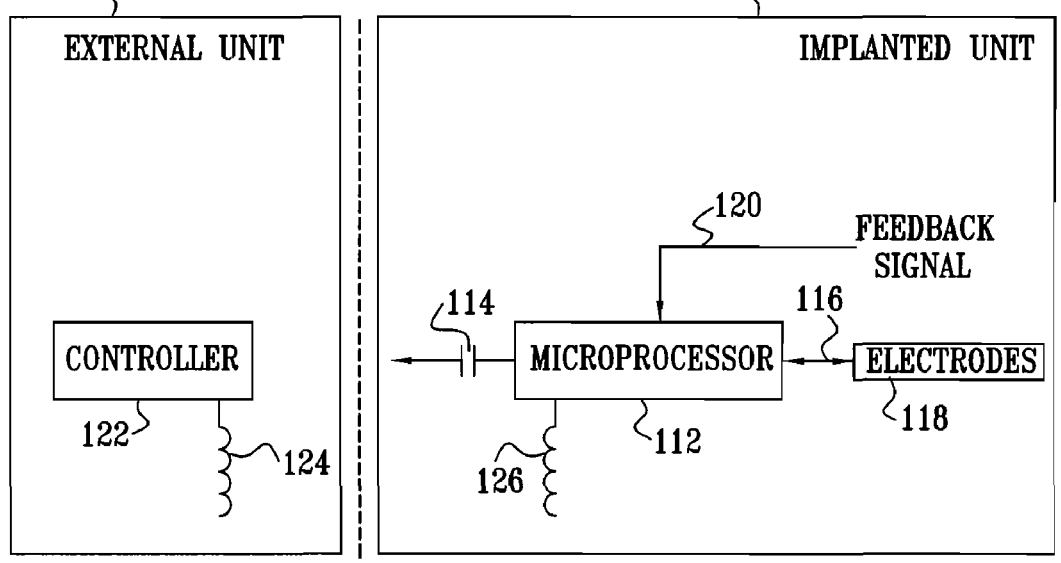
FIG. 9 is a schematic illustration of further apparatus for stimulation of the otic-ganglion site, in accordance with an embodiment of the present invention.

FIG. 9 is a schematic illustration of further apparatus for stimulation of the otic-ganglion site, in accordance with an embodiment of the present invention. In this embodiment, substantially all of the processing and signal generation is performed by circuitry in an implanted unit 110 in the patient, and, typically, communication with a controller 122 in an external unit 111 is performed only intermittently. The implanted unit 110 typically comprises a microprocessor 112 coupled to a battery 114. Microprocessor 112 generates a signal 116 that travels along at least one electrode 118 to stimulate the otic-ganglion site. A feedback signal 120 from a biosensor (not shown) and/or from electrode 118 is received by microprocessor 112, which is adapted to modify stimulation parameters responsive thereto. Typically, microprocessor 112 and controller 122 are operative to communicate via electromagnetic couplers 126 and 124, in order to exchange data or to change parameters. Further typically, battery 114 is inductively rechargeable by electromagnetic coupling.

Figure 10A:
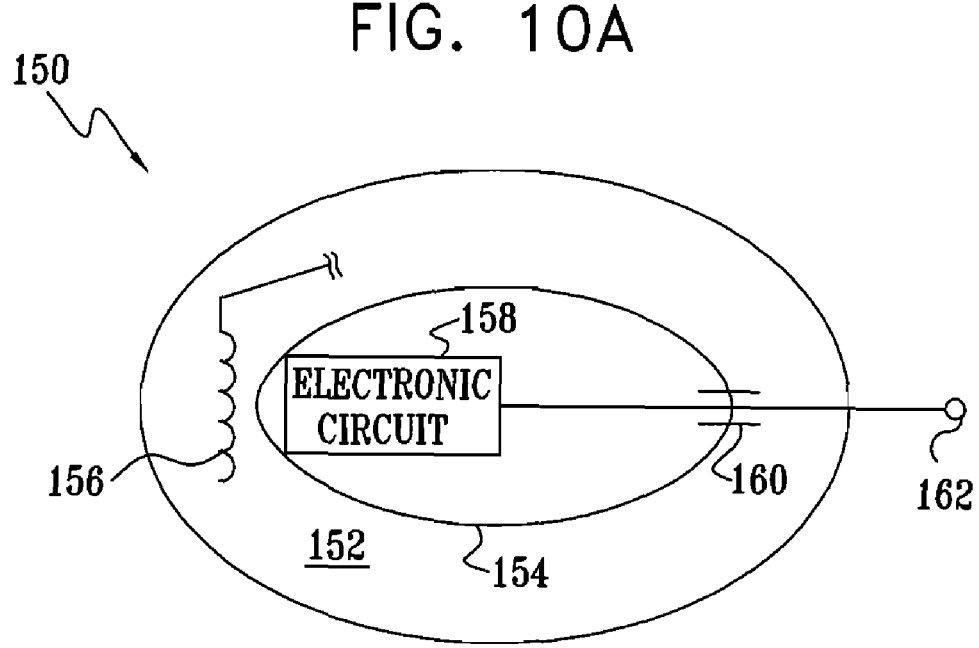
FIG. 10A is a schematic illustration of a stimulator, in accordance with an embodiment of the present invention.

FIG. 10A is a schematic illustration of a stimulator 150, in accordance with an embodiment of the present invention. Typically, substantially all of the electronic components (including an electronic circuit 158 having a rechargeable energy source) are encapsulated in a biocompatible metal case 154. An inductive coil 156 and at least one electrode 162 are typically coupled to circuit 158 by means of a feedthrough coupling 160. The inductive coil is typically isolated by an epoxy coating 152, which allows for higher efficiency of the electromagnetic coupling.

Figure 10B:
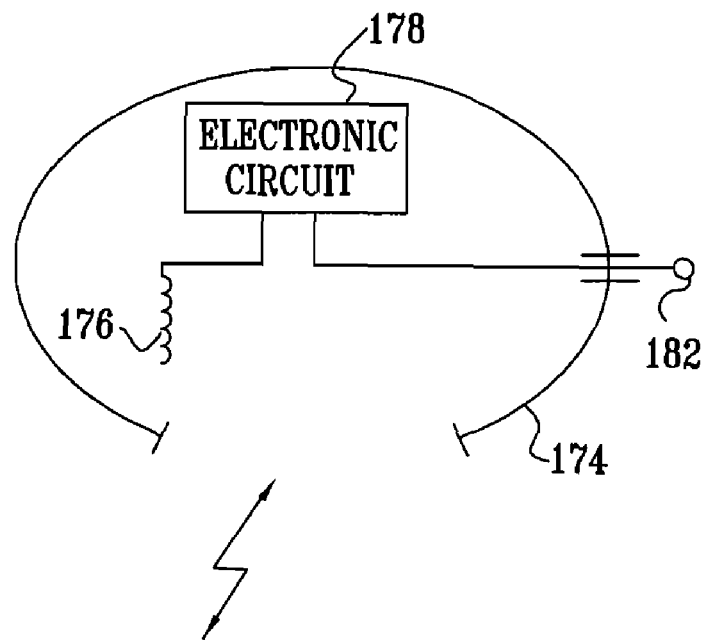
FIG. 10B is a schematic illustration of another configuration of an implantable stimulator, in accordance with an embodiment of the present invention.

FIG. 10B is a schematic illustration of another configuration of an implantable stimulator, in accordance with an embodiment of the present invention. Typically, substantially all of the electronic components (including an inductive coil 176 and an electronic circuit 178 having a rechargeable energy source) are encapsulated in a biocompatible metal case 174. One or more feed-throughs are typically provided to enable coupling between at least one electrode 182 and the electronic circuit, as well as between inductive coil 176 and another inductive coil (not shown) in communication therewith.

With reference to FIGS. 10A and 10B, the energy source for electronic circuits 158 and 178 may comprise, for example, a primary battery, a rechargeable battery, or a super capacitor. For applications in which a rechargeable battery or a super capacitor is used, any kind of energizing means may be used to charge the energy source, such as (but not limited to) standard means for inductive charging or a miniature electromechanical energy converter that converts the kinetics of the patient movement into electrical charge. Alternatively, an external light source (e.g., a simple LED, a laser diode, or any other light source) may be directed at a photovoltaic cell in the electronic circuit. Further alternatively, ultrasound energy is directed onto the implanted unit, and transduced to drive battery charging means.

In some embodiments, techniques described herein are practiced in combination with techniques described in one or both of the following co-assigned US applications: (i) U.S. patent application Ser. No. 10/294,310, filed Nov. 14, 2002, and a corresponding PCT application claiming priority therefrom, filed on even date herewith, entitled, "Stimulation for treating eye pathologies," and (ii) U.S. Provisional Patent Application 60/426,182, filed Nov. 14, 2002, entitled, "Stimulation circuitry and control of electronic medical device." All of these applications are incorporated herein by reference.

In an embodiment of the present invention, the stimulator is configured to configure the applied current to block the otic-ganglion site. For example, if CBF is high because of irregularly high activity of the parasympathetic tracts, blocking of the otic-ganglion site may be performed to bring the blood flow back to normal values. It is hypothesized that this will be effective in the cases such as migraine, which are related to over-excitability of the parasympathetic system.

In some embodiments of the present invention, techniques described herein are practiced in combination with techniques described in one or more of the references cited in the Background of the Invention section hereinabove and/or in combination with techniques described in one or more of the patent applications cited hereinabove.

The scope of the present invention includes embodiments described in the following patent applications, which are assigned to the assignee of the present patent application and are incorporated herein by reference. In an embodiment of the present invention, techniques and apparatus described in one or more of the following applications are combined with techniques and apparatus described herein:

U.S. Provisional Patent Application 60/203,172, filed May 8, 2000, entitled, "Method and apparatus for stimulating the sphenopalatine ganglion to modify properties of the BBB and cerebral blood flow"

U.S. patent application Ser. No. 10/258,714, filed Oct. 25, 2002, entitled, "Method and apparatus for stimulating the sphenopalatine ganglion to modify properties of the BBB and cerebral blood flow," or the above-referenced PCT Publication WO 01/85094

U.S. Provisional Patent Application 60/364,451, filed Mar. 15, 2002, entitled, "Applications of stimulating the sphenopalatine ganglion (SPG)"

U.S. Provisional Patent Application 60/368,657, filed Mar. 28, 2002, entitled, "SPG Stimulation"

U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head"

U.S. Provisional Patent Application 60/388,931, filed Jun. 14, 2002, entitled "Methods and systems for management of Alzheimer's disease," PCT Patent Application PCT/IL03/000508, filed Jun. 13, 2003, claiming priority therefrom, and a U.S. patent application filed Dec. 14, 2004 in the national stage thereof U.S. Provisional Patent Application 60/400,167, filed Jul. 31, 2002, entitled, "Delivering compounds to the brain by modifying properties of the BBB and cerebral circulation"

U.S. Provisional Patent Application 60/426,180, filed Nov. 14, 2002, entitled, "Surgical tools and techniques for sphenopalatine ganglion stimulation," PCT Patent Application PCT/IL03/000966, filed Nov. 13, 2003, which claims priority therefrom, and a U.S. patent application filed May 11, 2005 in the national stage thereof U.S. Provisional Patent Application 60/426,182, filed Nov. 14, 2002, and corresponding PCT Patent Application PCT/IL03/000967, which claims priority therefrom, filed Nov. 13, 2003, entitled, "Stimulation circuitry and control of electronic medical device," and a U.S. patent application filed May 11, 2005 in the national stage thereof U.S. patent application Ser. No. 10/294,310, filed Nov. 14, 2002, entitled, "SPG stimulation for treating eye pathologies," which published as US Patent Application Publication 2003/0176898, and PCT Patent Application PCT/IL03/000965, filed Nov. 13, 2003, claiming priority therefrom PCT Patent Application PCT/IL03/000631, filed Jul. 31, 2003, entitled, "Delivering compounds to the brain by modifying properties of the BBB and cerebral circulation," which published as PCT Publication WO 04/010923, and U.S. patent application Ser. No. 10/522,615 in the national stage thereof U.S. Pat. No. 6,853,858 to Shalev U.S. patent application Ser. No. 10/783,113, filed Feb. 20, 2004, entitled, "Stimulation for acute conditions," which published as US Patent Application Publication 2004/0220644

U.S. Provisional Patent Application 60/426,181, filed Nov. 14, 2002, entitled, "Stimulation for treating ear pathologies," PCT Patent Application PCT/IL03/000963, filed Nov. 13, 2003, which claims priority therefrom, and which published as PCT Publication WO 04/045242, and U.S. patent application Ser. No. 10/535,025 in the national stage thereof U.S. Provisional Patent Application 60/448,807, filed Feb. 20, 2003, entitled, "Stimulation for treating autoimmune-related disorders of the CNS"

U.S. Provisional Patent Application 60/461,232 to Gross et al., filed Apr. 8, 2003, entitled, "Treating abnormal conditions of the mind and body by modifying properties of the blood-brain barrier and cephalic blood flow"

PCT Patent Application PCT/IL03/00338 to Shalev, filed Apr. 25, 2003, entitled, "Methods and apparatus for modifying properties of the BBB and cerebral circulation by using the neuroexcitatory and/or neuroinhibitory effects of odorants on nerves in the head," and U.S. patent application Ser. No. 10/512,780, filed Oct. 25, 2004 in the national stage thereof, which published as US Patent Application 2005/0266099

U.S. Provisional Patent Application 60/506,165, filed Sep. 26, 2003, entitled, "Diagnostic applications of stimulation"

U.S. patent application Ser. No. 10/678,730, filed Oct. 2, 2003, entitled, "Targeted release of nitric oxide in the brain circulation for opening the BBB," which published as US Patent Application 2005/0074506, and PCT Patent Application PCT/IL04/000911, filed Oct. 3, 2004, claiming priority therefrom PCT Patent Application PCT/IL04/000897, filed Sep. 26, 2004, entitled, "Stimulation for treating and diagnosing conditions," which published as PCT Publication WO 05/030025

U.S. Provisional Patent Application 60/604,037, filed Aug. 23, 2004, entitled, "Concurrent bilateral SPG modulation"

PCT Patent Application PCT/IL05/000912, filed Aug. 23, 2005, entitled, "Concurrent bilateral SPG modulation," which published as PCT Publication WO 06/021957

U.S. patent application Ser. No. 10/952,536, filed Sep. 27, 2004, entitled, "Stimulation for treating and diagnosing conditions," which published as US Patent Application Publication 2005/0159790

U.S. patent application Ser. No. 11/349,020, filed Feb. 7, 2006, entitled, "SPG stimulation via the greater palatine canal"

U.S. patent application Ser. No. 11/465,381, filed Aug. 17, 2006, entitled, "Stimulation for treating brain events and other conditions"

Typically, methods of embodiments of the present invention comprise identifying that a patient suffers from at least one condition (such as at least one of those conditions mentioned hereinabove), and, responsively to the identifying, treating the condition by applying electrical stimulation to the otic-ganglion site. More generally, methods of embodiments of the present invention typically comprise identifying that a patient may benefit from a change in CBF and/or in BBB permeability, such as an increase or decrease in CBF and/or an increase or decrease in BBB permeability, and, responsively to the identifying, applying electrical stimulation to the otic-ganglion site. The benefit of such changes is typically the treatment of at least one condition of the subject, such as at least one of those conditions mentioned hereinabove.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
one or more electrodes, adapted to be applied to an otic-ganglion site of a patient selected from the group consisting of: an otic ganglion, an associated neural tract of the otic ganglion, an afferent fiber going into the otic ganglion, and an efferent fiber going out of the otic ganglion; and
a stimulator, configured to:
drive the one or more electrodes to apply a current to the otic-ganglion site, and
configure the current to activate the otic-ganglion site sufficiently to induce at least one effect selected from the group consisting of: a change in cerebral blood flow (CBF) of the patient, and a change in permeability of a blood-brain-barrier (BBB) of the patient.

2. The apparatus according to claim 1, wherein the stimulator is configured to configure the current to activate the otic-ganglion site sufficiently to induce an increase in the CBF.

3. The apparatus according to claim 2, wherein the stimulator is configured to configure the current to activate the otic-ganglion site sufficiently to treat stroke of the patient, by inducing the increase in the CBF.

4. The apparatus according to claim 2, wherein the stimulator is configured to configure the current to activate the otic-ganglion site sufficiently to treat a condition of the patient, by inducing the increase in the CBF, the condition selected from the group consisting of: depression, and anxiety.

5. The apparatus according to claim 1, wherein the stimulator is configured to configure the current to activate the otic-ganglion site sufficiently to induce an increase in BBB permeability.

6. The apparatus according to claim 5, wherein the stimulator is configured to configure the current to activate the otic-ganglion site sufficiently to facilitate drug transport across the BBB, by inducing the increase in BBB permeability.

7. The apparatus according to claim 1, wherein the stimulator is configured to configure the current to control properties of posterior cephalic circulation.

8. The apparatus according to claim 1, wherein the stimulator is configured to drive the one or more electrodes to apply the current on a long-term basis.

9. The apparatus according to claim 1, wherein the otic-ganglion site includes the otic ganglion, wherein the one or more electrodes are adapted to be applied to the otic ganglion, and wherein the stimulator is configured to drive the one or more electrodes to apply the current to the otic ganglion.

10. The apparatus according to claim 1, wherein the otic-ganglion site includes the associated neural tract of the otic ganglion, wherein the one or more electrodes are adapted to be applied to the associated neural tract of the otic ganglion, and wherein the stimulator is configured to drive the one or more electrodes to apply the current to the associated neural tract of the otic ganglion.

11. The apparatus according to claim 1, wherein the otic-ganglion site is selected from the group consisting of: the afferent fiber going into the otic ganglion, and the efferent fiber going out of the otic ganglion, wherein the one or more electrodes are adapted to be applied to the selected site, and wherein the stimulator is configured to drive the one or more electrodes to apply the current to the selected site.

12. The apparatus according to claim 1, wherein the stimulator is configured to be implanted in a body of the patient.

13. The apparatus according to claim 1, wherein the stimulator comprises circuitry, which comprises:
an implantable unit, configured to be implanted in a body of the patient, the implantable unit comprising an implantable unit coupler; and
an external unit, comprising an external unit coupler configured to be wirelessly coupled to the implantable unit coupler, the external unit configured to convey a control signal from the external unit coupler to the implantable unit coupler, which signal drives the implantable unit to drive the electrodes to apply the current to the site.

14. The apparatus according to claim 1, wherein the one or more electrodes are adapted for a period of implantation in the patient of greater than about one month.

15. The apparatus according to claim 1, wherein the one or more electrodes are adapted for a period of implantation in the patient of less than one week.

16. The apparatus according to claim 1, wherein the stimulator is configured to drive the one or more electrodes by wireless communication from a position external to the patient.

17. The apparatus according to claim 1, wherein the stimulator is configured to configure the current to activate the otic-ganglion site sufficiently to treat a condition of the patient selected from the group consisting of: a brain tumor, epilepsy, Parkinson's disease, Alzheimer's disease, multiple sclerosis, schizophrenia, and stress.

18. A method comprising:
selecting an otic-ganglion site of a patient from the group consisting of: an otic ganglion, an associated neural tract of the otic ganglion, an afferent fiber going into the otic ganglion, and an efferent fiber going out of the otic ganglion; and
applying a current to the otic-ganglion site, and configuring the current to activate the site sufficiently to induce at least one effect selected from the group consisting of: a change in cerebral blood flow (CBF) of the patient, and a change in permeability of a blood-brain-barrier (BBB) of the patient.

19. The method according to claim 18, comprising identifying that the patient may benefit from the at least one effect, wherein applying the current comprises applying the current responsively to the identifying.

20. The method according to claim 18, wherein configuring the current comprises configuring the current to activate the otic-ganglion site sufficiently to induce an increase in the CBF.

21. The method according to claim 20, wherein configuring the current comprises configuring the current to activate the otic-ganglion site sufficiently to treat stroke of the patient, by inducing the increase in the CBF.

22. The method according to claim 20, wherein configuring the current comprises configuring the current to activate the otic-ganglion site sufficiently to treat a condition of the patient, by inducing the increase in the CBF, the condition selected from the group consisting of: depression, and anxiety.

23. The method according to claim 18, wherein configuring the current comprises configuring the current to activate the otic-ganglion site sufficiently to induce an increase in BBB permeability.

24. The method according to claim 23, wherein configuring the current comprises configuring the current to activate the otic-ganglion site sufficiently to facilitate drug transport across the BBB, by inducing the increase in BBB permeability.

25. The method according to claim 18, wherein configuring the current comprises configuring the current to control properties of posterior cephalic circulation.

26. The method according to claim 18, wherein applying the current comprises applying the current on a long-term basis.

27. The method according to claim 18, wherein the otic-ganglion site includes the otic ganglion, and wherein applying the current comprises applying the current to the otic ganglion.

28. The method according to claim 18, wherein the otic-ganglion site includes the associated neural tract of the otic ganglion, and wherein applying the current comprises applying the current to the associated neural tract of the otic ganglion.

29. The method according to claim 18, wherein the otic-ganglion site is selected from the group consisting of: the afferent fiber going into the otic ganglion, and the efferent fiber going out of the otic ganglion, and wherein applying the current comprises applying the current to the selected site.

30. The method according to claim 18, wherein applying the current comprises implanting a stimulator in a body of the patient, and applying the current by the stimulator.

31. The method according to claim 18, wherein applying the current comprises:
wirelessly conveying a control signal from a position external to a body of the patient;
receiving the control signal at a position within the body; and
responsively to the received control signal, applying the current to the site.

32. The method according to claim 18, wherein applying the current comprises implanting one or more electrodes for a period of implantation in the patient of greater than about one month, and driving the one or more electrodes to apply the current.

33. The method according to claim 18, wherein applying the current comprises implanting one or more electrodes for a period of implantation in the patient of less than one week, and driving the one or more electrodes to apply the current.

34. The method according to claim 18, wherein applying the current comprises implanting one or more electrodes, and driving the one or more electrodes, by wireless communication from a position external to the patient, to apply the current to the site.

35. The method according to claim 18, wherein configuring the current comprises configuring the current to activate the otic-ganglion site sufficiently to treat a condition of the patient selected from the group consisting of: a brain tumor, epilepsy, Parkinson's disease, Alzheimer's disease, multiple sclerosis, schizophrenia, and stress.

\* \* \* \* \*